(12) United States Patent
Ward et al.

(10) Patent No.: US 6,177,245 B1
(45) Date of Patent: Jan. 23, 2001

(54) MANIPULATION OF PROTOPORPHYRINOGEN OXIDASE ENZYME ACTIVITY IN EUKARYOTIC ORGANISMS

(75) Inventors: Eric R. Ward, Basel (CH); Sandra Volrath, Durham, NC (US)

(73) Assignee: Novartis Finance Corporation, New York, NY (US)

( * ) Notice: Under 35 U.S.C. 154(b), the term of this patent shall be extended for 0 days.

(21) Appl. No.: 09/071,296

(22) Filed: May 1, 1998

Related U.S. Application Data

(63) Continuation-in-part of application No. 08/261,198, filed on Jun. 16, 1994, now abandoned.

(51) Int. Cl.[7] .............................. C12Q 1/68; C07H 21/04; C07H 21/02

(52) U.S. Cl. ............................ 435/6; 536/23.1; 536/24.3; 536/24.31; 536/24.34

(58) Field of Search ................................ 435/6; 536/23.1, 536/24.3, 24.31, 24.32

(56) References Cited

U.S. PATENT DOCUMENTS

| | | | |
|---|---|---|---|
| 5,407,808 | 4/1995 | Halling et al. | 435/34 |
| 5,451,513 | 9/1995 | Maliga et al. | 435/172.3 |
| 5,530,191 | 6/1996 | Maliga et al. | 800/205 |
| 5,545,817 | 8/1996 | McBride et al. | 800/205 |
| 5,576,198 | 11/1996 | McBride et al. | 435/91.3 |
| 5,693,507 | 12/1997 | Daniell et al. | 435/172.3 |
| 5,767,373 | 6/1998 | Ward et al. | 800/205 |

FOREIGN PATENT DOCUMENTS

| | | |
|---|---|---|
| 0 332 104 | 9/1989 | (EP) . |
| 0 360 750 | 9/1989 | (EP) . |
| 0 449 376 | 10/1991 | (EP) . |
| 0 478 502 A2 | 4/1992 | (EP) . |
| 0 479 359 | 4/1992 | (EP) . |
| 0 589 841 | 3/1994 | (EP) . |
| WO90/06748 | 6/1990 | (WO) . |
| WO91/16440 | 10/1991 | (WO) . |
| WO91/19418 | 12/1991 | (WO) . |
| WO92/01042 | 1/1992 | (WO) . |
| WO 9219731 * | 11/1992 | (WO) . |
| WO95/14099 | 5/1995 | (WO) . |
| WO95/16783 | 6/1995 | (WO) . |
| WO95/20668 | 8/1995 | (WO) . |
| WO95/25787 | 9/1995 | (WO) . |
| WO95/34659 | 12/1995 | (WO) . |
| WO96/04781 | 2/1996 | (WO) . |
| WO97/04088 | 2/1997 | (WO) . |
| WO97/04089 | 2/1997 | (WO) . |
| WO97/06250 | 2/1997 | (WO) . |
| WO97/32011 | 2/1997 | (WO) . |
| WO97/32977 | 9/1997 | (WO) . |

OTHER PUBLICATIONS

Al–Hazimi et al., "Synthetic and Biosynthetic Studies of Porphyrins Part 7. The Action of Coproporphyrinogen Oxidase on Coproporphyrinogen IV: Syntheses of Protoporphyrin XIII, mesoporphyrin XIII, and Related Tricarboxylic Porphyrins", J Chem Soc P Trans. 1 (1987), (2), 265–76.

Allison et al. "Deletion of rpoB reveals a second distinct transcription system in plastids of higher plants" The EMBO Journal, 15:2802–2809 (1996).

Armbruster et al., "Herbicidal Action of Nitrophenyl Pryazole Ether MON 12800: Immunolocalization, Ultrastructural, and Physiological Studies", Pestice Biochemistry and Physiology, 47: 21–35 (1993).

Aspegren et al., "Secretion of a heat–stable fungal beta–glucanase from transgenic suspension–cultured barley cells," Molecular Breeding, 1: 91–99 (1995).

Becerril et al., "Acifluorfen Effects on Intermediates of Chlorophyll Synthesis in Green Cucumber Cotyledon Tissues", Pesticide Biochemistry and Physiology, 35: 119–126 (1989).

Bilang et al., "Containing excitement over transplastomic plants," Nature Biotechnology, 16: 333–334 (1998).

Brenner et al., "Cloning of murine ferrocheletase", Proc. Natl. Acad. Sci. USA 88: 849–853 (1991).

Brenner et al., "A Fluorometric Assay for Measurement of Protoporphyrinogen Oxidase Activity in Mammalian Tissue", Clinica Chimica Acta, 100: 259–266 (1980).

Camadro et al., "A New Assay for Protoporphyrinogen Oxidase—Evidence for a Total Deficiency in that Activity in a Heme–Less Mutant of *Saccharomyces cerevisiae*", Biochemical and Biophysical Research Communications, 106(3): 724–730 (1982).

(List continued on next page.)

* cited by examiner

Primary Examiner—Jeffrey Fredman
Assistant Examiner—Juliet C. Einsmanh
(74) Attorney, Agent, or Firm—Edouard G. Lebel; J. Timothy Meigs; Larry W. Stults

(57) ABSTRACT

The present invention provides novel eukaryotic DNA sequences coding for native protoporphyrinogen oxidase (protox) or modified forms of the enzyme which are herbicide tolerant. Plants having altered protox activity which confers tolerance to herbicides are also provided. These plants may be bred or engineered for resistance to protox inhibitors via mutation of the native protox gene to a resistant form or through increased levels of expression of the native protox gene, or they may be transformed with modified eukaryotic or prokaryotic protox coding sequences or wild type prokaryotic protox sequences which are herbicide tolerant. Diagnostic and other uses for the novel eukaryotic protox sequence are also described. Plant genes encoding wild-type and altered protox, purified plant protox, methods of isolating protox from plants, and methods of using protox-encoding genes are also disclosed.

7 Claims, No Drawings

OTHER PUBLICATIONS

Camadro et al., "Cloning and Characterization of the Yeast HEM14 Gene Codoing for Protoporphyrinogen Oxidase, the Molecular Target of Diphenyl Ether–type Herbicides", The Journal of Biological Chemistry, 271(15): 9120–9128 (1996).

Camadro et al., "Molecular Properties of Yeast and Lettuce Protoporphyrinogen Oxidases", Abstract Pap Am Chem. Soc., 111. (1–2) (1993).

Camadro et al., "Photoaffinity labeling of protoporphyrinogen oxidase, the molecular target of diphenylether–type herbicides", Eur J of Biochem., 229: 669–674 (1995).

Camadro et al., "Purification and Properties of Protoporphyrinogen Oxidase from the Yeast *Saccharomyces cerevisiae*: Mitochondrial Location and Evidence for a Precursor Form of the Protein", The Journal of Biological Chemistry, 269(51): 32085–91 (1994).

Cardin et al., "Characterization of Protoporphyrinogen Oxidase from Rhodopseudomonas capsulata", Abstracts of the Annual Meeting Am. Soc. Microbiol., Abstract #K–85, 207 (1986).

Che et al., "Localization of Target–Site of the Protoporphyrinogen Oxidase–Inhibiting Herbicide S–23142 in *Spinacia–oleracea* L.", Z. Naturforsch., 48(c): 350–355 (1993).

Clarke et al. "Identification and expression of the chloroplast clpP gene in the conifer *Pinus contorta*" Plant Molecular Biology, 26: 851–862 (1994).

Corrigall et al., "Inhibition of Mammalian Protoporphyrinogen Oxidase by Acifluorfen", Biochemistry and Molecular Biology International, 34(6): 1283–1289 (1994).

Crews et al., "Synthesis and Herbicidal Activity of bis–Aryloxybenzenes, A New Class of Protox Inhibitors", Abstracts of Papers American Chemical Society, Abstract #044. 209(1–2) (1995).

Dailey et al., "Expression of a Cloned Protoporphyrinogen Oxidase", The Journal of Biological Chemistry, 269(2):813–815 (1994).

Dailey T.A. et al., "Cloning, Sequence, and Expression of Mouse Protoporphyrinogen Oxidase", Archives of Biochemistry and Biophysics, 324(2): 379–384 (1995).

Dailey T.A. et al., "Human protoporphyrinogen oxidase: Expression, purification, and characterization of the cloned enzyme", Protein Science, 5: 98–105 (1996).

Daniell et al., "Containment of herbicide resistance through genetic engineering of the chloroplast genome," Nature Biotechnology, 16: 345–348 (1998).

Datta et al., "Transformation of the Tobacco Chloroplast Genome with the aroA Gene to Confer Glyphosate Tolerance," Supplements to Plant Physiology, 111(2): 790 (1996).

Derrick, Peter Michael, "An Investigation into the mode of action of the herbicide M&B 39279", Dissertation Abstracts International, 50(10): 4283–B (1996).

Deybach et al., "The mitochondrial location of protoporphyrinogen oxidase", Eur. J. Biochem., 149(2): 431–436 (1985).

Duke et al., "Porphyric Pesticides Chemistry, Toxicology, and Pharmaceutical Applications", ACS Symposium Series 559, American Chemical Society, 1–318 (1994).

Duke et al., "Protoporphyrinogen Oxidase–Inhibiting Herbicides", Weed Science, 39: 465–473 (1991).

Duke et al., "Protoporphyrinogen Oxidase as the Optimal Herbicide Site in the Porphyrin Pathway", ACS Symp. Ser.—Porphyric Pesticides 191–204 (1994).

Duke et al., "Prospects for Herbicides Designed for Sites of Action in the Porphyrin Pathway Beyond Protoporphyrinogen Oxidase", Abstracts of Papers American Chemical Society, Abstract #129, 206(1–2) (1993).

Duke, S.O., "Pesticides that Act Through Prophyrin Accumulation", Abstracts of the 22nd Annual Meeting of the American Society for Photobiology, Abstract #SPM–B2, 59 (Spec. Issue) (1994).

Elder et al., "A Radiochemical Method for the Measurement of Coproporphyrinogen Oxidase and the Utilization of Substrates other than Coproporphyrinogen III by the Enzyme from Rat Liver", Biochem. J., 169: 205–214 (1978).

Ems et al. "Transcription, splicing and editing of plastid RNAs in the nonphotosynthetic plant *Epifagus virginiana*" Plant Molecular Biology, 29: 721–733 (1995).

EMBL Sequence Database Acc. No. M22063 Rel. 19 Apr. 22, 1989.

EMBL Sequence Database Acc. No. T43573, Rel. No. 42, Feb. 3, 1995.

Falbel et al., "Characterization of a Family of Chlorophyll–Deficient Wheat (Triticum) and Barley (*Hordeum vulgare*) Mutants with Defects in the Magnesium–Insertion Step of Chlorophyll Biosynthesis", Plant Physiology (Rockville), 104: 639–648 (1994).

Ferreira et al., "Organization of the Terminal Two Enzymes of the Heme Biosynthetic Pathway Orientation of Protoporphyrinogen Oxidase and Evidence for a Membrane Complex*", The Journal of Biolocial Chemistry, 263(8): 3835–3839 (1988).

Frustaci et al., "The *Escherichia–coli* vis A Gene Encodes Ferrochelatase, the Final Enzyme of the Heme Biosynthetic Pathway", Journal of Bacteriology, 175(7): 2154–2156 (1993).

Gollub et al., "Yeast Mutants Deficient in Heme Biosynthesis and a Heme Mutant Additionally Blocked in Cyclization of 2 3 Oxidosqualene*", The Journal of Biological Chemistry, 252(9): 2846–2854 (1977).

Guo et al., "High–performance liquid chromatographic assays for protoporphyrinogen oidase and ferrochelatase in human leukocytes", Journal of Chromatography Biomedical Applications, 566: 383–396 (1991).

Hallahan et al., "Mode of Action Studies on a Chiral Diphenyl Ether Peroxidizing Herbicide Correlation between Differential Inhibition of Protoporphyrinogen IX Oxidase Activity and Induction of Tetrapyrrole Accumulation by the Enantiomers", Plant Physiol. (1992) 100(3) 1211–16.

Hansson et al., "*Bacillus subtilis* Hem Y Is a Peripheral Membrane Protein Essential for Protoheme IX Synthesis Which Can Oxidize Coproporphyrinogen III and Protoporphyrinogen IX", Journal of Bacteriology, 176(19): 5962–5970 (1994).

Hansson et al., "Cloning and Characterization of the *Bacillus subtilis* hemEHY Gene Cluster, Which Encodes Protoheme IX Biosynthetic Enzymes", J. Bacteriol. 174(24) 8081–8093 (1992).

Heifetz et al., "Chemical regulation of nuclear and plastid transgenes in plants," Supplement to Plant Physiology, 114(3): 308 (1997).

Huang et al. "The Chlamydomonas chloroplast clpP gene contains translated large insertion sequences and is essential for cell growth" Mol Gen Genet, 244: 151–159 (1994).

Inchinose et al., "Selection and Characterization of Protoporphyrinogen Oxidase Inhibiting Herbicide (S23142) Resistant Photomixotrophic Cultured Cells of *Nicotiana tabacum*", J. Plant Physiol., 146: 693–698 (1995).

Ihara et al., "Peroxidizing Phytotoxic Activity of 1,3,4–Thiadiazolidine–2–thiones and 1,2,4–Triazolidine–3,5–dithiones", Journal of Pesticide Science, 20: 41–47 (1995).

Iida et al., "Isomerization and Peroxidizing Phytotoxicity of Thiadiazolidine–thione Compounds", Z. Naturforsch., 50(c): 186–192 (1995).

International Search Report PCT/IB 95/00452.

Jacobs et al., "Effect of Diphenyl Ether Herbicides on Oxidation of Protoporphyrinogen to Protoporphyrin in Organellar and Plasma Membrane Enriched Fractions of Barley", Plant Physiol. (Bethesda), 97: 197–203 (1991).

Jacobs et al., "Oxidation of protoporphyrinogen to protoporphyrin, a step in chlorophyll and haem biosynthesis", Biochem J., 244: 219–224 (1987).

Jacobs et al., "Porphyrin Accumulation and Export by Isolated Barley (*Hordeum–vulgare*) Plastids. Effect of Diphenyl Ether Herbicides", Plant Physiol. (ROCKV), 101: 1181–1188 (1993).

Jacobs J. M. et al., "Terminal Enzymes of Heme Biosynthesis in the Plant Plasma Membrane", Archives of Biochemistry and Biophysics, 323(2): 274–278 (1995).

Jacobs J.M. et al., "Effects of Diphenyl Dther Herbicides on Porphyrin Accumulation by Cultured Hepatocytes", J. Biochem. Toxicology, 7(2): 87–95 (1992).

Jacobs J.M. et al., "Effects of the Photobleaching Herbicide, Acifluorfen–methyl, on Protoporphyrinogen Oxidation in Barley Organelles, Soybean Root Mitochondria Soybean Root Nodules, and Bacteria", Archives of Biochemistry and Biophysics, 280(2): 369–375 (1990).

Jacobs J.M. et al., "Protoporphyrinogen Oxidation, an Enzymatic Step in Heme and Chlorophyll Synthesis: Partial Characterization of the Reaction in Plant Organelles and Comparison with Mammalian and Bacterial Systems1", Archives of Biochem and Biophys, 229(1): 312–319 (1984).

Jacobs N. et al., "Protoporphyrinogen oxidation in plants and rhizobia", Plant Physiol. (Bethesda), #1055 (4 Suppl.) (1989).

Jacobs N.J. et al., "Assay for Enzymatic Protoporphyrinogen Oxidation, a Late Step in Heme Synthesis", Enzyme (Basel), 28: 206–217 (1982).

Jacobs N.J. et al., "Characteristics of Purified Protoporphyrinogen Oxidase from Barley", Biochemical and Biophysical Research Communications, 161(2): 790–796 (1989).

Jacobs N.J. et al., "Mechanisms of Protoporphyrin IX Accumulation in Plant Cells Treated with Herbicides Inhibiting Protoporphyrinogen Oxidase", Abstract PAP Am. Chem. Soc., Abstract#113, 206(1–2) (1993).

Jacobs N.J. et al. "Microbial Oxidation of Protoporphyrinogen an Intermediate in Heme and Chlorophyll Biosynthesis", Archives of Biochemistry and Biophysics, 197(2): 396–403 (1979).

Jacobs N.J. et al., "Protoporphyrinogen Oxidation, a Step in Heme Synthesis in Soybean Root Nodules and Free–Living Rhizobia", Journal of Bacteriology, 171(1): 573–576 (1989).

Jansen et al., "Mode of Evolved Photooxidant Resistance to Herbicides and Xenobiotics", Z. Naturforsch Sect. Biosci., 45(c): 463–469 (1990).

Kataoka et al., "Isolation and Partial Characterization of Mutant Chlamydomas reinhardtii Resistant to Herbicide S–23142", J. Pesticide Sci., 15:499–451(1990).

Klemm et al., "Protoporphyrinogen oxidation coupled to nitrite reduction with membranes from Desulfovibrio–gigas", FEMS Microbiology Letters, 61: 61–64 (1989).

Klemm et al., "Purification and Properties of Protoporphyrinogen Oxidase from an Anaerobic Bacterium, Desulfovibrio–gigas", Journal of Bacteriology, 169(11): 5209–5215 (1987).

Kohno et al., "Peroxidizing Phytotoxic Activity of Pyrazoles", Journal of Pesticide Science, 20: 137–143 (1995).

Kolarov et al., "Rat Liver Protoporphyrinogen IX Oxidase: Site of Synthesis and Factor Influencing Its Activity", Biochemical and Biophysical Research Communications, 116(2): 383–387 (1983).

Komives et al, "Mechanisms of Plant Tolerance to Phytodynamic Herbicides", Abstract PAP Am. Chem. Soc., Abstract#128, 206(1–2) (1993).

Koop et al. "Integration of foreign sequences into the tobacco plastome via polyethylene glycol–mediated protoplast transformation" Planta, 199: 193–201 (1996).

Labbe–Bois R., "The Ferrochetelase from *Saccharomyces–Cerevisiae*. Sequence, Disruption, and Expression of Its Structural Gene HEM15*", The Journal of Biological Chemistry, 265(13): 7278–7283 (1990).

Labbe et al., "Fluorometric assays for coproporphyrinogen oxidase and protoporphyrinogen oxidase", Analytical Biochemistry, 149: 248–260 (1985).

Lee et al., "Cellular Localization of Protoporphyrinogen–Oxidizing Activities of Etiolated Barley (*Hordeum vulgare* L.) Leaves", Plant Physiol., 102:881–889 (1993).

Lee et al., "Peroxidase Involvement in the Accumulation of Protoporphyrin IX in Acifluorfen–Methyl–Treated Plant Tissues", Plant Physiology (Rockville), 105(1 Suppl.): 125 (1994).

Lee H.J. et al., "Protoporphyrinogen IX–Oxidizing Activities Involved in the Mode of Action of Peroxidizing Herbicides", Journal of Agricultural and Food Chemistry, 42(11): 2610–2618 (1994).

Li et al., "An h.p.l.c. assay for protoporphyrinogen oxidase activity in rat liver", Biochem. J., 243: 863–866 (1987).

Lyga et al., "Synthesis, Mechanism of Action, and QSAR of Herbicidal 3–Substituted–2–aryl–4,5,6,7–tetrahydroindazoles", Pesticide Science, 42: 29–36 (1994).

Madsen et al., "A soybean coproporphyrinogen oxidase gene is highly expressed in root nodules", Plant Molecular Biology, 23: 35–43, (1993).

Martasek et al., "Homozygous hereditary coproporphyria caused by an arginine to tryptophan substitution in coproporphyrinogen oxidase and common intragenic polymorphisms", Human Molecular Genetics, 3(3): 477–480 (1994).

Martasek et al., "Molecular cloning, sequencing, and functional expression of a cDNA encoding human coproporphyrinogen oxidase", Proceedings of the National Academy of Sciences of the United States of America, 91: 3024–3028 (1994).

Matringe et al., "Characterization of [3H]acifluorfen binding to purified pea etioplasts, and evidence that protoporphyrinogen oxidase specifically binds acifluorfen", Eur. J. Biochem., 209: 861–868 (1992).

Matringe et al., "Localization within Chloroplasts of Protoporphyrinogen Oxidase, the Target Enzyme for Diphenylether–like Herbicides", The Journal of Biological Chemistry, 267(7):4646–4651 (1992).

Matringe et al., "Protoporphyrinogen oxidase as a molecular target for diphenyl ether herbicides", Biochem. J., 260:231–235 (1989).

Matringe et al., "Protoporphyrinogen oxidase inhibition by three peroxidizing herbicides: oxadiazon, LS 82–556 and M&B 39279", FEBS Letters, 245(1,2): 35–38 (1989).

Matsumoto et al., "A Rapid and Strong Inhibition of Protoporphyrinogen Oxidase from Several Plant Species by Oxyfluorfen", Pesticide Biochemistry and Physiology, 47: 113–118 (1993).

Matsumoto et al., "Variation in Crop Response to Protoporphyrinogen Oxidase Inhibitors", Abstract. PAP Am. Chem. Soc., Abstract#124, 206 (1–2) (1993).

McBride et al., "Controlled expression of plastid transgenes in plants based on a nuclear DNA–encoded and plastid–targeted T7 RNA polymerase," Proc.Natl. Acad. Sci., 91: 7301–7305 (1994).

Mullet, John E., "Dynamic Regulation of Chloroplast Transcription", Plant Physiology, 103: 309–313 (1993).

Nakayashiki et al., "Cloning and sequencing of a previously unidentified gene that is involved in the biosynthesis of heme in *Escherichia coli*", Gene (Amsterdam), 153: 67–70 (1995).

Nandihalli et al., "Correlation of Protoporphyrinogen Oxidase Inhibition by O–Phenyl Pyrrolidino–and Piperidino–Carbamates with their Herbicidal Effects", Pestic. Sci., 35: 227–235 (1992).

Nandihalli et al., "Enantioselectivity of Protoporphyrinogen Oxidase–Inhibiting Herbicides", Pesticide Science, 40: 265–277 (1994).

Nandihalli et al., "Relationships between Molecular Properties and Biological Activities of O–Phenyl Pyrrolidino–and Piperidinocarbamate Herbicides", J. Agri. Food Chem., 40(10): 1993–2000 (1992).

Nandihalli et al., "The Porphyrin Pathway as a H Ervicide Target Site", Abstract#140 PAP Am. Chem. Soc., 203 (1992).

Nicolaus et al., "Binding Affinities of Peroxidizing Herbicides to Protoporphyrinogen Oxidase from Corn", Pesticide Biochemistry and Physiology, 51: 20–29 (1995).

Nicolaus et al., "Molecular Aspects of Herbicide Action on Protoporphyrinogen Oxidase", Z. Naturforsch, 48(c): 326–333 (1993).

Nishimura et al., "Cloning of a Human cDNA for Protoporphyrinogen Oxidase by Complementation in Vivo of a hemG Mutant of *Escherichia coli*", J. of Biological Chemistry, 270(14): 8076–8080 (1995).

O'Neill et al. "Chloroplast transformation in plants: polyethylene glycol (PEG) treatment of protoplasts is an alternative to biolistic delivery systems" The Plant Journal, 3(5): 729–738 (1993).

Oshio et al., "Isolation and Characterization of a *Chlamydomonas reinhardtii* Mutant Resistant to Photobleaching Herbicides", Z. Naturforsch. 48c: 339–344 (1993).

Pen et al., "Production of Active *Bacillus Licheniformis* Alpha–Amylase in Tobacco and its Application in Starch Liquefaction," Bio/Technology, 10(3): 292–296 (1992).

Pornprom et al., "Characterizaiton of Oxyfluorfen Tolerance in Selected Soybean Cell Line", Pesticide Biochemistry and Physiology 50: 107–114 (1994).

Pornprom et al., "Selection for Herbicide Tolerance in Soybean Using Cell Suspension Culture", Weed Research, 39(2): 102–108 (1994).

Prasad A.R.K. et al., "Generation of Resistance to the Diphenyl Ether Herbicide Acifluorfen by Mel Cells*", Biochemical and Biophysical Research Communications, 215(1): 186–191 (1995).

Proulx et al., "Characteristics of murine protoporphyrinogen oxidase", Protein Science, 1: 801–809 (1992).

Proulx et al., "In situ conversion of coproporphyrinogen to heme by murine mitochondria: Terminal steps of the heme biosynthetic pathway", Protein Science, 2: 1092–1098 (1993).

Reddy K.N., "Modulators of the Porphyrin Pathway Beyond Protox", Abstract PAP Am. Chem. Soc., Abstract#127, 206(1–2) (1993).

Roberts et al., "Partial characterization and assignment of the gene for protoporphyrinogen oxidase and variegate porphyria to human chromosome 1q23", Human Molecular Genetics, 4(12): 2387–2390 (1995).

Sasarman et al., "Nucleoside sequence of the hemG gene involved in the protoporphyrinogen oxidase activity of *Escherichia coli* K12", Can. J. Microbiol., 39:1155–1161 (1993).

Sato et al., "Isomerization and Peroxidizing Phytotoxicity of Thiadiazolidine Herbicides", Z. Naturforsch., 49(c): 49–56 (1994).

Scalla et al., "Inhibitors of Protoporphyrinogen Oxidase as Herbicides: Diphenyl Ethers and Related Photobleaching Molecules", Reviews of Weed Science, 6: 103–132 (1994).

Shanklin et al. "The Stroma of Higher Plant Plastids Contain ClpP and ClpC, Functional Homologs of *Escherichia coli* ClpP andClpA: An Archetypal Two–Component ATP–Dependent Protease" The Plant Cell, 7: 1713–1722 (1995).

Sherman et al., "Physiological Basis for Differential Sensitivities of Plant Species to Protoporphyrinogen Oxidase–Inhibiting Herbicides", Plant Physiol. 97: 280–287 (1991).

Sherman et al., "Pyrazole Phenyl Ether Herbicides Inhibit Protoporphyrinogen Oxidase", Pesticide Biochemistry and Physiology, 40: 236–245 (1991).

Sherman et al., "Tissue and Cellular Localization of Porphyrins in Cucumber Cotyledon Tissue with Inhibited Protoporphyrinogen Oxidase", Plant Physiol. (Bethesda), 93 (1Suppl.) (1990).

Shibata et al., "Isolation and Characterization of a Chlamydomonas reinhardtii Mutant Resistant to an Experimental Herbicide S–23142, Which Inhibits Chlorophyll Synthesis", Research in Photosynthesis, III:567–570 (1992).

Shimizu et al., "A Novel Isourazole Herbicide, Fluthiacet–Methyl, is a Potent Inhibitor of Protoporphyrinogen Oxidase after Isomerization by Glutathione S–Transferase", Plant and Cell Physiology, 36(4): 625–632 (1995).

Siepker et al., "Purification of bovine protoporphyrinogen oxidase: immunological cross–reactivity and structural relationship ferrochelatase", Biochimica et Biophysica Acta, 931: 349–358 (1987).

Smith et al., "Investigaton of the subcellular location of the tetrapyrrole–biosynthesis enzyme coproporphyrinogen oxidase in higher plants", Biochem. J., 292: 503–508 (1993).

Sriraman "In vivo characterisation of a promoter for the nucleus encoded plastid RNA polymerase" New York Area Plant Molecular Biology Meeting, (1998).

Staub et al., "Long Regions og Homologous DNA Are Incorporated into the Tobacco Plastid Genome by Transformation", The Plant Cell, 4: 39–45 (1992).

Struhl, "They new yeast genetics", Nature 305:3 91–397 (1983).

Svab et al. "High–frequency plastid transformation in tobacco by selection for a chimeric aadA gene" Proc. Natl. Acad. Sci. USA, 90: 913–917 (1993).

Taketani et al., "The Human Protoporphyrinogen Oxidase Gene (PPOX): Organization and Location to Chromosome 1", Genomics, 29: 698–703 (1995).

Tietjen K.G., "Quinone Activation of Protoporphyrinogen Oxidase of Barley Plastids", Pestic. Sci., 33: 467–471 (1991).

Tonkyn et al., "Differential expression of the partially duplicated chloroplast S10 ribosomal operon", Mol Gen Genet, 241: 141–152 (1993).

Troup et al., "Cloning and Characterization of the *Escherichia coli* hemN Gene Encoding the Oxygen–Independent Coproporphyrinogen III Oxidase", Journal of Bacteriology, 177(11): 3326–3331 (1995).

Troup et al., "Isolation of the hemF Operon Containing the Gene for the *Escherichia coli* Aerobic Coproporphyrinogen III Oxidase by In Vivo Complementation of a Yeast HEM13 Mutant", Journal of Bacteriology, 176(3): 673–680 (1994).

Varsano et al., "Competitive interaction of three peroxidizing herbicides with the binding of [3 H]acifluorfen to corn etioplast membranes", FEBS, 272(1,2): 106–108 (1990).

Viljoen et al., "Protoporphyrinogen oxidase and ferrochelatase in porphyria variegata", European Journal of Clinical Investigation, 13: 283–287 (1983).

Wang et al., "New Assay Method for Protoporphyrinogen Oxidase Inhibitors Using Chloroplasts Isolated from *Spinacia oleracea* L", Bioscience Biotechnology and Biochemistry, 57(12): 2205–2206 (1993).

Wepplo et al., "Synthesis and Herbicidal Activity of 5–Aryloxybenzisoxazole–3–Acetate Esters", Abstr. Pap. Am. Chem. Soc., Abstract#16, 205(1–2) (1993).

Witkowski et al., "Inhibition of Plant Protoporphyrinogen Oxidase by the Herbicide Acifluorfen–Methyl", Plant Physiol. (Bethesda), 90: 1239–1242 (1989).

Wright et al., "Herbicidal Activity of UCC–C4243 and Acifluorfen Is Due to Inhibition of Protoporphyrinogen Oxidase", Weed Science, 43: 47–54 (1995).

Xu et al., "An Oxygen–Dependent Coproporphyringoen Oxidase Encoded by the hemF Gene of *Salmonella–typhimurium*", Journal of Bacteriology, 175(16): 4990–4999 (1993).

Xu et al., "The Genes Required for Heme Synthesis in *Salmonella–typhimurium* Include Those Encoding Alternative Functions for Aerobic and Anaerobic Coproporphyrinogen Oxidation", Journal of Bacteriology, 174(12): 3953–3963 (1992).

Yamato et al., "A Tobacco Soluble Protoporphyrinogen–oxidizing Enzyme Similar to Plant Peroxidases in Their Amino Acid Sequences and Immunochemical Reactivity", Bioscience Biotechnology and Biochemistry, 59(3): 558–559 (1995).

Yamato et al., "Purification and characterization of a protoporphyrinogen–oxidizing enzyme with peroxidase activity and light–dependent herbicide resistance in tobacco cultured cells", Pestic. Biochem. Physiol., 50: 72–82 (1994).

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1719 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 31..1644
      (D) OTHER INFORMATION: /note= "Arabidopsis protox-1 cDNA;
         sequence from pWDC-2"

(xi) SEQUENCE DESCRIPTION: SEQ ID NO:1:

```
TGACAAAATT CCGAATTCTC TGCGATTTCC ATG GAG TTA TCT CTT CTC CGT CCG        54
                                Met Glu Leu Ser Leu Leu Arg Pro
                                  1               5

ACG ACT CAA TCG CTT CTT CCG TCG TTT TCG AAG CCC AAT CTC CGA TTA        102
Thr Thr Gln Ser Leu Leu Pro Ser Phe Ser Lys Pro Asn Leu Arg Leu
```

```
                  10                      15                       20
AAT GTT TAT AAG CCT CTT AGA CTC CGT TGT TCA GTG GCC GGT GGA CCA         150
Asn Val Tyr Lys Pro Leu Arg Leu Arg Cys Ser Val Ala Gly Gly Pro
 25                  30                      35                      40

ACC GTC GGA TCT TCA AAA ATC GAA GGC GGA GGA GGC ACC ACC ATC ACG         198
Thr Val Gly Ser Ser Lys Ile Glu Gly Gly Gly Gly Thr Thr Ile Thr
                 45                      50                      55

ACG GAT TGT GTG ATT GTC GGC GGA GGT ATT AGT GGT CTT TGC ATC GCT         246
Thr Asp Cys Val Ile Val Gly Gly Gly Ile Ser Gly Leu Cys Ile Ala
                     60                      65                      70

CAG GCG CTT GCT ACT AAG CAT CCT GAT GCT GCT CCG AAT TTA ATT GTG         294
Gln Ala Leu Ala Thr Lys His Pro Asp Ala Ala Pro Asn Leu Ile Val
             75                      80                      85

ACC GAG GCT AAG GAT CGT GTT GGA GGC AAC ATT ATC ACT CGT GAA GAG         342
Thr Glu Ala Lys Asp Arg Val Gly Gly Asn Ile Ile Thr Arg Glu Glu
         90                      95                     100

AAT GGT TTT CTC TGG GAA GAA GGT CCC AAT AGT TTT CAA CCG TCT GAT         390
Asn Gly Phe Leu Trp Glu Glu Gly Pro Asn Ser Phe Gln Pro Ser Asp
105                     110                     115                    120

CCT ATG CTC ACT ATG GTG GTA GAT AGT GGT TTG AAG GAT GAT TTG GTG         438
Pro Met Leu Thr Met Val Val Asp Ser Gly Leu Lys Asp Asp Leu Val
                    125                     130                     135

TTG GGA GAT CCT ACT GCG CCA AGG TTT GTG TTG TGG AAT GGG AAA TTG         486
Leu Gly Asp Pro Thr Ala Pro Arg Phe Val Leu Trp Asn Gly Lys Leu
                140                     145                     150

AGG CCG GTT CCA TCG AAG CTA ACA GAC TTA CCG TTC TTT GAT TTG ATG         534
Arg Pro Val Pro Ser Lys Leu Thr Asp Leu Pro Phe Phe Asp Leu Met
            155                     160                     165

AGT ATT GGT GGG AAG ATT AGA GCT GGT TTT GGT GCA CTT GGC ATT CGA         582
Ser Ile Gly Gly Lys Ile Arg Ala Gly Phe Gly Ala Leu Gly Ile Arg
170                     175                     180

CCG TCA CCT CCA GGT CGT GAA GAA TCT GTG GAG GAG TTT GTA CGG CGT         630
Pro Ser Pro Pro Gly Arg Glu Glu Ser Val Glu Glu Phe Val Arg Arg
185                     190                     195                    200

AAC CTC GGT GAT GAG GTT TTT GAG CGC CTG ATT GAA CCG TTT TGT TCA         678
Asn Leu Gly Asp Glu Val Phe Glu Arg Leu Ile Glu Pro Phe Cys Ser
                    205                     210                     215

GGT GTT TAT GCT GGT GAT CCT TCA AAA CTG AGC ATG AAA GCA GCG TTT         726
Gly Val Tyr Ala Gly Asp Pro Ser Lys Leu Ser Met Lys Ala Ala Phe
                220                     225                     230

GGG AAG GTT TGG AAA CTA GAG CAA AAT GGT GGA AGC ATA ATA GGT GGT         774
Gly Lys Val Trp Lys Leu Glu Gln Asn Gly Gly Ser Ile Ile Gly Gly
            235                     240                     245

ACT TTT AAG GCA ATT CAG GAG AGG AAA AAC GCT CCC AAG GCA GAA CGA         822
Thr Phe Lys Ala Ile Gln Glu Arg Lys Asn Ala Pro Lys Ala Glu Arg
250                     255                     260

GAC CCG CGC CTG CCA AAA CCA CAG GGC CAA ACA GTT GGT TCT TTC AGG         870
Asp Pro Arg Leu Pro Lys Pro Gln Gly Gln Thr Val Gly Ser Phe Arg
265                     270                     275                    280

AAG GGA CTT CGA ATG TTG CCA GAA GCA ATA TCT GCA AGA TTA GGT AGC         918
Lys Gly Leu Arg Met Leu Pro Glu Ala Ile Ser Ala Arg Leu Gly Ser
                    285                     290                     295

AAA GTT AAG TTG TCT TGG AAG CTC TCA GGT ATC ACT AAG CTG GAG AGC         966
Lys Val Lys Leu Ser Trp Lys Leu Ser Gly Ile Thr Lys Leu Glu Ser
                300                     305                     310

GGA GGA TAC AAC TTA ACA TAT GAG ACT CCA GAT GGT TTA GTT TCC GTG        1014
Gly Gly Tyr Asn Leu Thr Tyr Glu Thr Pro Asp Gly Leu Val Ser Val
            315                     320                     325

CAG AGC AAA AGT GTT GTA ATG ACG GTG CCA TCT CAT GTT GCA AGT GGT        1062
```

```
Gln Ser Lys Ser Val Val Met Thr Val Pro Ser His Val Ala Ser Gly
            330                 335                 340

CTC TTG CGC CCT CTT TCT GAA TCT GCT GCA AAT GCA CTC TCA AAA CTA      1110
Leu Leu Arg Pro Leu Ser Glu Ser Ala Ala Asn Ala Leu Ser Lys Leu
345                 350                 355                 360

TAT TAC CCA CCA GTT GCA GCA GTA TCT ATC TCG TAC CCG AAA GAA GCA      1158
Tyr Tyr Pro Pro Val Ala Ala Val Ser Ile Ser Tyr Pro Lys Glu Ala
                365                 370                 375

ATC CGA ACA GAA TGT TTG ATA GAT GGT GAA CTA AAG GGT TTT GGG CAA      1206
Ile Arg Thr Glu Cys Leu Ile Asp Gly Glu Leu Lys Gly Phe Gly Gln
            380                 385                 390

TTG CAT CCA CGC ACG CAA GGA GTT GAA ACA TTA GGA ACT ATC TAC AGC      1254
Leu His Pro Arg Thr Gln Gly Val Glu Thr Leu Gly Thr Ile Tyr Ser
                395                 400                 405

TCC TCA CTC TTT CCA AAT CGC GCA CCG CCC GGA AGA ATT TTG CTG TTG      1302
Ser Ser Leu Phe Pro Asn Arg Ala Pro Pro Gly Arg Ile Leu Leu Leu
410                 415                 420

AAC TAC ATT GGC GGG TCT ACA AAC ACC GGA ATT CTG TCC AAG TCT GAA      1350
Asn Tyr Ile Gly Gly Ser Thr Asn Thr Gly Ile Leu Ser Lys Ser Glu
425                 430                 435                 440

GGT GAG TTA GTG GAA GCA GTT GAC AGA GAT TTG AGG AAA ATG CTA ATT      1398
Gly Glu Leu Val Glu Ala Val Asp Arg Asp Leu Arg Lys Met Leu Ile
                445                 450                 455

AAG CCT AAT TCG ACC GAT CCA CTT AAA TTA GGA GTT AGG GTA TGG CCT      1446
Lys Pro Asn Ser Thr Asp Pro Leu Lys Leu Gly Val Arg Val Trp Pro
                460                 465                 470

CAA GCC ATT CCT CAG TTT CTA GTT GGT CAC TTT GAT ATC CTT GAC ACG      1494
Gln Ala Ile Pro Gln Phe Leu Val Gly His Phe Asp Ile Leu Asp Thr
                475                 480                 485

GCT AAA TCA TCT CTA ACG TCT TCG GGC TAC GAA GGG CTA TTT TTG GGT      1542
Ala Lys Ser Ser Leu Thr Ser Ser Gly Tyr Glu Gly Leu Phe Leu Gly
490                 495                 500

GGC AAT TAC GTC GCT GGT GTA GCC TTA GGC CGG TGT GTA GAA GGC GCA      1590
Gly Asn Tyr Val Ala Gly Val Ala Leu Gly Arg Cys Val Glu Gly Ala
505                 510                 515                 520

TAT GAA ACC GCG ATT GAG GTC AAC AAC TTC ATG TCA CGG TAC GCT TAC      1638
Tyr Glu Thr Ala Ile Glu Val Asn Asn Phe Met Ser Arg Tyr Ala Tyr
                525                 530                 535

AAG TAAATGTAAA ACATTAAATC TCCCAGCTTG CGTGAGTTTT ATTAAATATT          1691
Lys

TTGAGATATC CAAAAAAAAA AAAAAAAA                                       1719

(2) INFORMATION FOR SEQ ID NO:2:

(i) SEQUENCE CHARACTERISTICS:
          (A) LENGTH: 537 amino acids
          (B) TYPE: amino acid
          (D) TOPOLOGY: linear (ii) MOLECULE TYPE: protein (xi) SEQUENCE DESCRIPTION: SEQ ID NO:2:

Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
                20                  25                  30

Arg Cys Ser Val Ala Gly Gly Pro Thr Val Gly Ser Ser Lys Ile Glu
            35                  40                  45

Gly Gly Gly Gly Thr Thr Ile Thr Thr Asp Cys Val Ile Val Gly Gly
        50                  55                  60
```

```
Gly Ile Ser Gly Leu Cys Ile Ala Gln Ala Leu Ala Thr Lys His Pro
 65                  70                  75                  80

Asp Ala Ala Pro Asn Leu Ile Val Thr Glu Ala Lys Asp Arg Val Gly
                 85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
    290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Leu Asn Tyr Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480
```

```
Gly His Phe Asp Ile Leu Asp Thr Ala Lys Ser Ser Leu Thr Ser Ser
            485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
            515                 520                 525

Asn Phe Met Ser Arg Tyr Ala Tyr Lys
            530                 535

(2) INFORMATION FOR SEQ ID NO:3:

(i) SEQUENCE CHARACTERISTICS:
        (A) LENGTH: 1738 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 70..1596
        (D) OTHER INFORMATION: /note= "Arabidopsis protox-2 cDNA;
            sequence from pWDC-1"

(xi) SEQUENCE DESCRIPTION: SEQ ID NO:3:

TTTTTTACTT ATTTCCGTCA CTGCTTTCGA CTGGTCAGAG ATTTTGACTC TGAATTGTTG         60

CAGATAGCA ATG GCG TCT GGA GCA GTA GCA GAT CAT CAA ATT GAA GCG            108
          Met Ala Ser Gly Ala Val Ala Asp His Gln Ile Glu Ala
            1               5                  10

GTT TCA GGA AAA AGA GTC GCA GTC GTA GGT GCA GGT GTA AGT GGA CTT          156
Val Ser Gly Lys Arg Val Ala Val Val Gly Ala Gly Val Ser Gly Leu
 15                  20                  25

GCG GCG GCT TAC AAG TTG AAA TCG AGG GGT TTG AAT GTG ACT GTG TTT          204
Ala Ala Ala Tyr Lys Leu Lys Ser Arg Gly Leu Asn Val Thr Val Phe
 30              35                  40                  45

GAA GCT GAT GGA AGA GTA GGT GGG AAG TTG AGA AGT GTT ATG CAA AAT          252
Glu Ala Asp Gly Arg Val Gly Gly Lys Leu Arg Ser Val Met Gln Asn
                 50                  55                  60

GGT TTG ATT TGG GAT GAA GGA GCA AAC ACC ATG ACT GAG GCT GAG CCA          300
Gly Leu Ile Trp Asp Glu Gly Ala Asn Thr Met Thr Glu Ala Glu Pro
             65                  70                  75

GAA GTT GGG AGT TTA CTT GAT GAT CTT GGG CTT CGT GAG AAA CAA CAA          348
Glu Val Gly Ser Leu Leu Asp Asp Leu Gly Leu Arg Glu Lys Gln Gln
         80                  85                  90

TTT CCA ATT TCA CAG AAA AAG CGG TAT ATT GTG CGG AAT GGT GTA CCT          396
Phe Pro Ile Ser Gln Lys Lys Arg Tyr Ile Val Arg Asn Gly Val Pro
     95                 100                 105

GTG ATG CTA CCT ACC AAT CCC ATA GAG CTG GTC ACA AGT AGT GTG CTC          444
Val Met Leu Pro Thr Asn Pro Ile Glu Leu Val Thr Ser Ser Val Leu
110                 115                 120                 125

TCT ACC CAA TCT AAG TTT CAA ATC TTG TTG GAA CCA TTT TTA TGG AAG          492
Ser Thr Gln Ser Lys Phe Gln Ile Leu Leu Glu Pro Phe Leu Trp Lys
                130                 135                 140

AAA AAG TCC TCA AAA GTC TCA GAT GCA TCT GCT GAA GAA AGT GTA AGC          540
Lys Lys Ser Ser Lys Val Ser Asp Ala Ser Ala Glu Glu Ser Val Ser
            145                 150                 155

GAG TTC TTT CAA CGC CAT TTT GGA CAA GAG GTT GTT GAC TAT CTC ATC          588
Glu Phe Phe Gln Arg His Phe Gly Gln Glu Val Val Asp Tyr Leu Ile
```

```
                    -continued 160                 165                 170
GAC CCT TTT GTT GGT GGA ACA AGT GCT GCG GAC CCT GAT TCC CTT TCA       636
Asp Pro Phe Val Gly Gly Thr Ser Ala Ala Asp Pro Asp Ser Leu Ser
    175                 180                 185

ATG AAG CAT TCT TTC CCA GAT CTC TGG AAT GTA GAG AAA AGT TTT GGC       684
Met Lys His Ser Phe Pro Asp Leu Trp Asn Val Glu Lys Ser Phe Gly
190                 195                 200                 205

TCT ATT ATA GTC GGT GCA ATC AGA ACA AAG TTT GCT GCT AAA GGT GGT       732
Ser Ile Ile Val Gly Ala Ile Arg Thr Lys Phe Ala Ala Lys Gly Gly
                210                 215                 220

AAA AGT AGA GAC ACA AAG AGT TCT CCT GGC ACA AAA AAG GGT TCG CGT       780
Lys Ser Arg Asp Thr Lys Ser Ser Pro Gly Thr Lys Lys Gly Ser Arg
            225                 230                 235

GGG TCA TTC TCT TTT AAG GGG GGA ATG CAG ATT CTT CCT GAT ACG TTG       828
Gly Ser Phe Ser Phe Lys Gly Gly Met Gln Ile Leu Pro Asp Thr Leu
        240                 245                 250

TGC AAA AGT CTC TCA CAT GAT GAG ATC AAT TTA GAC TCC AAG GTA CTC       876
Cys Lys Ser Leu Ser His Asp Glu Ile Asn Leu Asp Ser Lys Val Leu
    255                 260                 265

TCT TTG TCT TAC AAT TCT GGA TCA AGA CAG GAG AAC TGG TCA TTA TCT       924
Ser Leu Ser Tyr Asn Ser Gly Ser Arg Gln Glu Asn Trp Ser Leu Ser
270                 275                 280                 285

TGT GTT TCG CAT AAT GAA ACG CAG AGA CAA AAC CCC CAT TAT GAT GCT       972
Cys Val Ser His Asn Glu Thr Gln Arg Gln Asn Pro His Tyr Asp Ala
                290                 295                 300

GTA ATT ATG ACG GCT CCT CTG TGC AAT GTG AAG GAG ATG AAG GTT ATG      1020
Val Ile Met Thr Ala Pro Leu Cys Asn Val Lys Glu Met Lys Val Met
            305                 310                 315

AAA GGA GGA CAA CCC TTT CAG CTA AAC TTT CTC CCC GAG ATT AAT TAC      1068
Lys Gly Gly Gln Pro Phe Gln Leu Asn Phe Leu Pro Glu Ile Asn Tyr
        320                 325                 330

ATG CCC CTC TCG GTT TTA ATC ACC ACA TTC ACA AAG GAG AAA GTA AAG      1116
Met Pro Leu Ser Val Leu Ile Thr Thr Phe Thr Lys Glu Lys Val Lys
    335                 340                 345

AGA CCT CTT GAA GGC TTT GGG GTA CTC ATT CCA TCT AAG GAG CAA AAG      1164
Arg Pro Leu Glu Gly Phe Gly Val Leu Ile Pro Ser Lys Glu Gln Lys
350                 355                 360                 365

CAT GGT TTC AAA ACT CTA GGT ACA CTT TTT TCA TCA ATG ATG TTT CCA      1212
His Gly Phe Lys Thr Leu Gly Thr Leu Phe Ser Ser Met Met Phe Pro
                370                 375                 380

GAT CGT TCC CCT AGT GAC GTT CAT CTA TAT ACA ACT TTT ATT GGT GGG      1260
Asp Arg Ser Pro Ser Asp Val His Leu Tyr Thr Thr Phe Ile Gly Gly
            385                 390                 395

AGT AGG AAC CAG GAA CTA GCC AAA GCT TCC ACT GAC GAA TTA AAA CAA      1308
Ser Arg Asn Gln Glu Leu Ala Lys Ala Ser Thr Asp Glu Leu Lys Gln
        400                 405                 410

GTT GTG ACT TCT GAC CTT CAG CGA CTG TTG GGG GTT GAA GGT GAA CCC      1356
Val Val Thr Ser Asp Leu Gln Arg Leu Leu Gly Val Glu Gly Glu Pro
    415                 420                 425

GTG TCT GTC AAC CAT TAC TAT TGG AGG AAA GCA TTC CCG TTG TAT GAC      1404
Val Ser Val Asn His Tyr Tyr Trp Arg Lys Ala Phe Pro Leu Tyr Asp
430                 435                 440                 445

AGC AGC TAT GAC TCA GTC ATG GAA GCA ATT GAC AAG ATG GAG AAT GAT      1452
Ser Ser Tyr Asp Ser Val Met Glu Ala Ile Asp Lys Met Glu Asn Asp
                450                 455                 460

CTA CCT GGG TTC TTC TAT GCA GGT AAT CAT CGA GGG GGC CTC TCT GTT      1500
Leu Pro Gly Phe Phe Tyr Ala Gly Asn His Arg Gly Gly Leu Ser Val
            465                 470                 475

GGG AAA TCA ATA GCA TCA GGT TGC AAA GCA GCT GAC CTT GTG ATC TCA      1548
```

```
Gly Lys Ser Ile Ala Ser Gly Cys Lys Ala Ala Asp Leu Val Ile Ser
            480                 485                 490

TAC CTG GAG TCT TGC TCA AAT GAC AAG AAA CCA AAT GAC AGC TTA TAACATTG 1603
Tyr Leu Glu Ser Cys Ser Asn Asp Lys Lys Pro Asn Asp Ser Leu
        495                 500                 505

AAGGTTCGTC CCTTTTTATC ACTTACTTTG TAAACTTGTA AAATGCAACA AGCCGCCGTG      1663

CGATTAGCCA ACAACTCAGC AAAACCCAGA TTCTCATAAG GCTCACTAAT TCCAGAATAA      1723

ACTATTTATG TAAAA                                                      1738
```

(2) INFORMATION FOR SEQ ID NO:4:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Gly Ala Val Ala Asp His Gln Ile Glu Ala Val Ser Gly
 1               5                  10                  15

Lys Arg Val Ala Val Val Gly Ala Gly Val Ser Gly Leu Ala Ala Ala
                20                  25                  30

Tyr Lys Leu Lys Ser Arg Gly Leu Asn Val Thr Val Phe Glu Ala Asp
            35                  40                  45

Gly Arg Val Gly Gly Lys Leu Arg Ser Val Met Gln Asn Gly Leu Ile
        50                  55                  60

Trp Asp Glu Gly Ala Asn Thr Met Thr Glu Ala Glu Pro Glu Val Gly
 65                  70                  75                  80

Ser Leu Leu Asp Asp Leu Gly Leu Arg Glu Lys Gln Gln Phe Pro Ile
                85                  90                  95

Ser Gln Lys Lys Arg Tyr Ile Val Arg Asn Gly Val Pro Val Met Leu
            100                 105                 110

Pro Thr Asn Pro Ile Glu Leu Val Thr Ser Ser Val Leu Ser Thr Gln
        115                 120                 125

Ser Lys Phe Gln Ile Leu Leu Glu Pro Phe Leu Trp Lys Lys Lys Ser
130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                165                 170                 175

Val Gly Gly Thr Ser Ala Ala Asp Pro Asp Ser Leu Ser Met Lys His
            180                 185                 190

Ser Phe Pro Asp Leu Trp Asn Val Glu Lys Ser Phe Gly Ser Ile Ile
        195                 200                 205

Val Gly Ala Ile Arg Thr Lys Phe Ala Ala Lys Gly Gly Lys Ser Arg
    210                 215                 220

Asp Thr Lys Ser Ser Pro Gly Thr Lys Lys Gly Ser Arg Gly Ser Phe
225                 230                 235                 240

Ser Phe Lys Gly Gly Met Gln Ile Leu Pro Asp Thr Leu Cys Lys Ser
                245                 250                 255

Leu Ser His Asp Glu Ile Asn Leu Asp Ser Lys Val Leu Ser Leu Ser
            260                 265                 270

Tyr Asn Ser Gly Ser Arg Gln Glu Asn Trp Ser Leu Ser Cys Val Ser
        275                 280                 285
```

```
His Asn Glu Thr Gln Arg Gln Asn Pro His Tyr Asp Ala Val Ile Met
    290                 295                 300
Thr Ala Pro Leu Cys Asn Val Lys Glu Met Lys Val Met Lys Gly Gly
305                 310                 315                 320
Gln Pro Phe Gln Leu Asn Phe Leu Pro Glu Ile Asn Tyr Met Pro Leu
                325                 330                 335
Ser Val Leu Ile Thr Thr Phe Thr Lys Glu Lys Val Lys Arg Pro Leu
            340                 345                 350
Glu Gly Phe Gly Val Leu Ile Pro Ser Lys Glu Gln Lys His Gly Phe
        355                 360                 365
Lys Thr Leu Gly Thr Leu Phe Ser Ser Met Met Phe Pro Asp Arg Ser
    370                 375                 380
Pro Ser Asp Val His Leu Tyr Thr Thr Phe Ile Gly Gly Ser Arg Asn
385                 390                 395                 400
Gln Glu Leu Ala Lys Ala Ser Thr Asp Glu Leu Lys Gln Val Val Thr
                405                 410                 415
Ser Asp Leu Gln Arg Leu Leu Gly Val Glu Gly Glu Pro Val Ser Val
            420                 425                 430
Asn His Tyr Tyr Trp Arg Lys Ala Phe Pro Leu Tyr Asp Ser Ser Tyr
        435                 440                 445
Asp Ser Val Met Glu Ala Ile Asp Lys Met Glu Asn Asp Leu Pro Gly
    450                 455                 460
Phe Phe Tyr Ala Gly Asn His Arg Gly Gly Leu Ser Val Gly Lys Ser
465                 470                 475                 480
Ile Ala Ser Gly Cys Lys Ala Ala Asp Leu Val Ile Ser Tyr Leu Glu
                485                 490                 495
Ser Cys Ser Asn Asp Lys Lys Pro Asn Asp Ser Leu
            500                 505
```

(2) INFORMATION FOR SEQ ID NO:5:

(i) SEQUENCE CHARACTERISTICS:
        (A) LENGTH: 1698 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..1453
        (D) OTHER INFORMATION: /note= "Maize protox-1 cDNA (not
            full-length); sequence from pWDC-4"

(xi) SEQUENCE DESCRIPTION: SEQ ID NO:5:

```
G AAT TCG GCG GAC TGC GTC GTG GTG GGC GGA GGC ATC AGT GGC CTC        46
  Asn Ser Ala Asp Cys Val Val Val Gly Gly Gly Ile Ser Gly Leu
  1               5                  10                  15

TGC ACC GCG CAG GCG CTG GCC ACG CGG CAC GGC GTC GGG GAC GTG CTT     94
Cys Thr Ala Gln Ala Leu Ala Thr Arg His Gly Val Gly Asp Val Leu
                20                  25                  30

GTC ACG GAG GCC CGC GCC CGC CCC GGC GGC AAC ATT ACC ACC GTC GAG     142
Val Thr Glu Ala Arg Ala Arg Pro Gly Gly Asn Ile Thr Thr Val Glu
            35                  40                  45

CGC CCC GAG GAA GGG TAC CTC TGG GAG GAG GGT CCC AAC AGC TTC CAG     190
Arg Pro Glu Glu Gly Tyr Leu Trp Glu Glu Gly Pro Asn Ser Phe Gln
```

|  |  |  |  |  |  |  |  |  |  |  |  |  |  |  |  |  |
|---|---|---|---|---|---|---|---|---|---|---|---|---|---|---|---|---|
|  |  |  | 50 |  |  |  |  | 55 |  |  |  |  | 60 |  |  |  |
| CCC | TCC | GAC | CCC | GTT | CTC | ACC | ATG | GCC | GTG | GAC | AGC | GGA | CTG | AAG | GAT | 238 |
| Pro | Ser | Asp | Pro | Val | Leu | Thr | Met | Ala | Val | Asp | Ser | Gly | Leu | Lys | Asp |  |
|  |  | 65 |  |  |  | 70 |  |  |  | 75 |  |  |  |  |  |  |
| GAC | TTG | GTT | TTT | GGG | GAC | CCA | AAC | GCG | CCG | CGT | TTC | GTG | CTG | TGG | GAG | 286 |
| Asp | Leu | Val | Phe | Gly | Asp | Pro | Asn | Ala | Pro | Arg | Phe | Val | Leu | Trp | Glu |  |
| 80 |  |  |  |  | 85 |  |  |  |  | 90 |  |  |  |  | 95 |  |
| GGG | AAG | CTG | AGG | CCC | GTG | CCA | TCC | AAG | CCC | GCC | GAC | CTC | CCG | TTC | TTC | 334 |
| Gly | Lys | Leu | Arg | Pro | Val | Pro | Ser | Lys | Pro | Ala | Asp | Leu | Pro | Phe | Phe |  |
|  |  |  |  | 100 |  |  |  |  | 105 |  |  |  |  | 110 |  |  |
| GAT | CTC | ATG | AGC | ATC | CCA | GGG | AAG | CTC | AGG | GCC | GGT | CTA | GGC | GCG | CTT | 382 |
| Asp | Leu | Met | Ser | Ile | Pro | Gly | Lys | Leu | Arg | Ala | Gly | Leu | Gly | Ala | Leu |  |
|  |  |  | 115 |  |  |  |  | 120 |  |  |  |  | 125 |  |  |  |
| GGC | ATC | CGC | CCG | CCT | CCA | GGC | CGC | GAA | GAG | TCA | GTG | GAG | GAG | TTC |  | 430 |
| Gly | Ile | Arg | Pro | Pro | Pro | Gly | Arg | Glu | Glu | Ser | Val | Glu | Glu | Phe |  |  |
|  |  | 130 |  |  |  |  | 135 |  |  |  |  | 140 |  |  |  |  |
| GTG | CGC | CGC | AAC | CTC | GGT | GCT | GAG | GTC | TTT | GAG | CGC | CTC | ATT | GAG | CCT | 478 |
| Val | Arg | Arg | Asn | Leu | Gly | Ala | Glu | Val | Phe | Glu | Arg | Leu | Ile | Glu | Pro |  |
|  | 145 |  |  |  |  | 150 |  |  |  |  | 155 |  |  |  |  |  |
| TTC | TGC | TCA | GGT | GTC | TAT | GCT | GGT | GAT | CCT | TCT | AAG | CTC | AGC | ATG | AAG | 526 |
| Phe | Cys | Ser | Gly | Val | Tyr | Ala | Gly | Asp | Pro | Ser | Lys | Leu | Ser | Met | Lys |  |
| 160 |  |  |  |  | 165 |  |  |  |  | 170 |  |  |  |  | 175 |  |
| GCT | GCA | TTT | GGG | AAG | GTT | TGG | CGG | TTG | GAA | GAA | ACT | GGA | GGT | AGT | ATT | 574 |
| Ala | Ala | Phe | Gly | Lys | Val | Trp | Arg | Leu | Glu | Glu | Thr | Gly | Gly | Ser | Ile |  |
|  |  |  |  | 180 |  |  |  |  | 185 |  |  |  |  | 190 |  |  |
| ATT | GGT | GGA | ACC | ATC | AAG | ACA | ATT | CAG | GAG | AGG | AGC | AAG | AAT | CCA | AAA | 622 |
| Ile | Gly | Gly | Thr | Ile | Lys | Thr | Ile | Gln | Glu | Arg | Ser | Lys | Asn | Pro | Lys |  |
|  |  |  | 195 |  |  |  |  | 200 |  |  |  |  | 205 |  |  |  |
| CCA | CCG | AGG | GAT | GCC | CGC | CTT | CCG | AAG | CCA | AAA | GGG | CAG | ACA | GTT | GCA | 670 |
| Pro | Pro | Arg | Asp | Ala | Arg | Leu | Pro | Lys | Pro | Lys | Gly | Gln | Thr | Val | Ala |  |
|  |  | 210 |  |  |  |  | 215 |  |  |  |  | 220 |  |  |  |  |
| TCT | TTC | AGG | AAG | GGT | CTT | GCC | ATG | CTT | CCA | AAT | GCC | ATT | ACA | TCC | AGC | 718 |
| Ser | Phe | Arg | Lys | Gly | Leu | Ala | Met | Leu | Pro | Asn | Ala | Ile | Thr | Ser | Ser |  |
|  | 225 |  |  |  |  | 230 |  |  |  |  | 235 |  |  |  |  |  |
| TTG | GGT | AGT | AAA | GTC | AAA | CTA | TCA | TGG | AAA | CTC | ACG | AGC | ATT | ACA | AAA | 766 |
| Leu | Gly | Ser | Lys | Val | Lys | Leu | Ser | Trp | Lys | Leu | Thr | Ser | Ile | Thr | Lys |  |
| 240 |  |  |  |  | 245 |  |  |  |  | 250 |  |  |  |  | 255 |  |
| TCA | GAT | GAC | AAG | GGA | TAT | GTT | TTG | GAG | TAT | GAA | ACG | CCA | GAA | GGG | GTT | 814 |
| Ser | Asp | Asp | Lys | Gly | Tyr | Val | Leu | Glu | Tyr | Glu | Thr | Pro | Glu | Gly | Val |  |
|  |  |  |  | 260 |  |  |  |  | 265 |  |  |  |  | 270 |  |  |
| GTT | TCG | GTG | CAG | GCT | AAA | AGT | GTT | ATC | ATG | ACT | ATT | CCA | TCA | TAT | GTT | 862 |
| Val | Ser | Val | Gln | Ala | Lys | Ser | Val | Ile | Met | Thr | Ile | Pro | Ser | Tyr | Val |  |
|  |  |  | 275 |  |  |  |  | 280 |  |  |  |  | 285 |  |  |  |
| GCT | AGC | AAC | ATT | TTG | CGT | CCA | CTT | TCA | AGC | GAT | GCT | GCA | GAT | GCT | CTA | 910 |
| Ala | Ser | Asn | Ile | Leu | Arg | Pro | Leu | Ser | Ser | Asp | Ala | Ala | Asp | Ala | Leu |  |
|  |  | 290 |  |  |  |  | 295 |  |  |  |  | 300 |  |  |  |  |
| TCA | AGA | TTC | TAT | TAT | CCA | CCG | GTT | GCT | GCT | GTA | ACT | GTT | TCG | TAT | CCA | 958 |
| Ser | Arg | Phe | Tyr | Tyr | Pro | Pro | Val | Ala | Ala | Val | Thr | Val | Ser | Tyr | Pro |  |
|  | 305 |  |  |  |  | 310 |  |  |  |  | 315 |  |  |  |  |  |
| AAG | GAA | GCA | ATT | AGA | AAA | GAA | TGC | TTA | ATT | GAT | GGG | GAA | CTC | CAG | GGC | 1006 |
| Lys | Glu | Ala | Ile | Arg | Lys | Glu | Cys | Leu | Ile | Asp | Gly | Glu | Leu | Gln | Gly |  |
| 320 |  |  |  |  | 325 |  |  |  |  | 330 |  |  |  |  | 335 |  |
| TTT | GGC | CAG | TTG | CAT | CCA | CGT | AGT | CAA | GGA | GTT | GAG | ACA | TTA | GGA | ACA | 1054 |
| Phe | Gly | Gln | Leu | His | Pro | Arg | Ser | Gln | Gly | Val | Glu | Thr | Leu | Gly | Thr |  |
|  |  |  |  | 340 |  |  |  |  | 345 |  |  |  |  | 350 |  |  |
| ATA | TAC | AGT | TCC | TCA | CTC | TTT | CCA | AAT | CGT | GCT | CCT | GAC | GGT | AGG | GTG | 1102 |
| Ile | Tyr | Ser | Ser | Ser | Leu | Phe | Pro | Asn | Arg | Ala | Pro | Asp | Gly | Arg | Val |  |
|  |  |  | 355 |  |  |  |  | 360 |  |  |  |  | 365 |  |  |  |
| TTA | CTT | CTA | AAC | TAC | ATA | GGA | GGT | GCT | ACA | AAC | ACA | GGA | ATT | GTT | TCC | 1150 |

-continued

```
Leu Leu Leu Asn Tyr Ile Gly Gly Ala Thr Asn Thr Gly Ile Val Ser
            370                 375                 380

AAG ACT GAA AGT GAG CTG GTC GAA GCA GTT GAC CGT GAC CTC CGA AAA      1198
Lys Thr Glu Ser Glu Leu Val Glu Ala Val Asp Arg Asp Leu Arg Lys
    385                 390                 395

ATG CTT ATA AAT TCT ACA GCA GTG GAC CCT TTA GTC CTT GGT GTT CGA      1246
Met Leu Ile Asn Ser Thr Ala Val Asp Pro Leu Val Leu Gly Val Arg
400                 405                 410                 415

GTT TGG CCA CAA GCC ATA CCT CAG TTC CTG GTA GGA CAT CTT GAT CTT      1294
Val Trp Pro Gln Ala Ile Pro Gln Phe Leu Val Gly His Leu Asp Leu
                420                 425                 430

CTG GAA GCC GCA AAA GCT GCC CTG GAC CGA GGT GGC TAC GAT GGG CTG      1342
Leu Glu Ala Ala Lys Ala Ala Leu Asp Arg Gly Gly Tyr Asp Gly Leu
            435                 440                 445

TTC CTA GGA GGG AAC TAT GTT GCA GGA GTT GCC CTG GGC AGA TGC GTT      1390
Phe Leu Gly Gly Asn Tyr Val Ala Gly Val Ala Leu Gly Arg Cys Val
        450                 455                 460

GAG GGC GCG TAT GAA AGT GCC TCG CAA ATA TCT GAC TTC TTG ACC AAG      1438
Glu Gly Ala Tyr Glu Ser Ala Ser Gln Ile Ser Asp Phe Leu Thr Lys
    465                 470                 475

TAT GCC TAC AAG TGATGAAAGA AGTGGAGCGC TACTTGTTAA TCGTTTATGT          1490
Tyr Ala Tyr Lys
480

TGCATAGATG AGGTGCCTCC GGGGAAAAAA AAGCTTGAAT AGTATTTTTT ATTCTTATTT    1550

TGTAAATTGC ATTTCTGTTC TTTTTTCTAT CAGTAATTAG TTATATTTTA GTTCTGTAGG    1610

AGATTGTTCT GTTCACTGCC CTTCAAAGA AATTTTATTT TTCATTCTTT TATGAGAGCT    1670

GTGCTACTTA AAAAAAAAAA AAAAAAAA                                       1698

(2) INFORMATION FOR SEQ ID NO:6:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO:6:

Asn Ser Ala Asp Cys Val Val Gly Gly Ile Ser Gly Leu Cys
1               5                   10                  15

Thr Ala Gln Ala Leu Ala Thr Arg His Gly Val Gly Asp Val Leu Val
            20                  25                  30

Thr Glu Ala Arg Ala Arg Pro Gly Gly Asn Ile Thr Thr Val Glu Arg
        35                  40                  45

Pro Glu Glu Gly Tyr Leu Trp Glu Glu Gly Pro Asn Ser Phe Gln Pro
    50                  55                  60

Ser Asp Pro Val Leu Thr Met Ala Val Asp Ser Gly Leu Lys Asp Asp
65                  70                  75                  80

Leu Val Phe Gly Asp Pro Asn Ala Pro Arg Phe Val Leu Trp Glu Gly
                85                  90                  95

Lys Leu Arg Pro Val Pro Ser Lys Pro Ala Asp Leu Pro Phe Phe Asp
            100                 105                 110

Leu Met Ser Ile Pro Gly Lys Leu Arg Ala Gly Leu Gly Ala Leu Gly
        115                 120                 125

Ile Arg Pro Pro Pro Gly Arg Glu Glu Ser Val Glu Phe Val
    130                 135                 140

Arg Arg Asn Leu Gly Ala Glu Val Phe Glu Arg Leu Ile Glu Pro Phe
```

```
145                 150                 155                 160
Cys Ser Gly Val Tyr Ala Gly Asp Pro Ser Lys Leu Ser Met Lys Ala
                165                 170                 175

Ala Phe Gly Lys Val Trp Arg Leu Glu Glu Thr Gly Gly Ser Ile Ile
                180                 185                 190

Gly Gly Thr Ile Lys Thr Ile Gln Glu Arg Ser Lys Asn Pro Lys Pro
                195                 200                 205

Pro Arg Asp Ala Arg Leu Pro Lys Pro Lys Gly Gln Thr Val Ala Ser
    210                 215                 220

Phe Arg Lys Gly Leu Ala Met Leu Pro Asn Ala Ile Thr Ser Ser Leu
225                 230                 235                 240

Gly Ser Lys Val Lys Leu Ser Trp Lys Leu Thr Ser Ile Thr Lys Ser
                245                 250                 255

Asp Asp Lys Gly Tyr Val Leu Glu Tyr Glu Thr Pro Glu Gly Val Val
                260                 265                 270

Ser Val Gln Ala Lys Ser Val Ile Met Thr Ile Pro Ser Tyr Val Ala
                275                 280                 285

Ser Asn Ile Leu Arg Pro Leu Ser Ser Asp Ala Ala Asp Ala Leu Ser
                290                 295                 300

Arg Phe Tyr Tyr Pro Pro Val Ala Ala Val Thr Val Ser Tyr Pro Lys
305                 310                 315                 320

Glu Ala Ile Arg Lys Glu Cys Leu Ile Asp Gly Glu Leu Gln Gly Phe
                325                 330                 335

Gly Gln Leu His Pro Arg Ser Gln Gly Val Glu Thr Leu Gly Thr Ile
                340                 345                 350

Tyr Ser Ser Ser Leu Phe Pro Asn Arg Ala Pro Asp Gly Arg Val Leu
                355                 360                 365

Leu Leu Asn Tyr Ile Gly Gly Ala Thr Asn Thr Gly Ile Val Ser Lys
    370                 375                 380

Thr Glu Ser Glu Leu Val Glu Ala Val Asp Arg Asp Leu Arg Lys Met
385                 390                 395                 400

Leu Ile Asn Ser Thr Ala Val Asp Pro Leu Val Leu Gly Val Arg Val
                405                 410                 415

Trp Pro Gln Ala Ile Pro Gln Phe Leu Val Gly His Leu Asp Leu Leu
                420                 425                 430

Glu Ala Ala Lys Ala Ala Leu Asp Arg Gly Gly Tyr Asp Gly Leu Phe
                435                 440                 445

Leu Gly Gly Asn Tyr Val Ala Gly Val Ala Leu Gly Arg Cys Val Glu
    450                 455                 460

Gly Ala Tyr Glu Ser Ala Ser Gln Ile Ser Asp Phe Leu Thr Lys Tyr
465                 470                 475                 480

Ala Tyr Lys (2) INFORMATION FOR SEQ ID NO:7:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(ix) FEATURE:
    (A) NAME/KEY: CDS
    (B) LOCATION: 64..1698
    (D) OTHER INFORMATION: /note= "Maize protox-2 cDNA;
        sequence from pWDC-3"

(xi) SEQUENCE DESCRIPTION: SEQ ID NO:7:

| | | | | | | | | | | | | | | | | | | |
|---|---|---|---|---|---|---|---|---|---|---|---|---|---|---|---|---|---|---|
| CTCTCCTACC | TCCACCTCCA | CGACAACAAG | CAAATCCCCA | TCCAGTTCCA | AACCCTAACT | | | | | | | | | | | | | 60 |

| CAA | ATG | CTC | GCT | TTG | ACT | GCC | TCA | GCC | TCA | TCC | GCT | TCG | TCC | CAT | CCT | | | 108 |
| | Met | Leu | Ala | Leu | Thr | Ala | Ser | Ala | Ser | Ser | Ala | Ser | Ser | His | Pro | | | |
| | 1 | | | | 5 | | | | | 10 | | | | | 15 | | | |

| TAT | CGC | CAC | GCC | TCC | GCG | CAC | ACT | CGT | CGC | CCC | CGC | CTA | CGT | GCG | GTC | | | 156 |
| Tyr | Arg | His | Ala | Ser | Ala | His | Thr | Arg | Arg | Pro | Arg | Leu | Arg | Ala | Val | | | |
| | | | | 20 | | | | | 25 | | | | | 30 | | | | |

| CTC | GCG | ATG | GCG | GGC | TCC | GAC | GAC | CCC | CGT | GCA | GCG | CCC | GCC | AGA | TCG | | | 204 |
| Leu | Ala | Met | Ala | Gly | Ser | Asp | Asp | Pro | Arg | Ala | Ala | Pro | Ala | Arg | Ser | | | |
| | | | 35 | | | | | 40 | | | | | 45 | | | | | |

| GTC | GCC | GTC | GTC | GGC | GCC | GGG | GTC | AGC | GGG | CTC | GCG | GCG | GCG | TAC | AGG | | | 252 |
| Val | Ala | Val | Val | Gly | Ala | Gly | Val | Ser | Gly | Leu | Ala | Ala | Ala | Tyr | Arg | | | |
| | | 50 | | | | | 55 | | | | | 60 | | | | | | |

| CTC | AGA | CAG | AGC | GGC | GTG | AAC | GTA | ACG | GTG | TTC | GAA | GCG | GCC | GAC | AGG | | | 300 |
| Leu | Arg | Gln | Ser | Gly | Val | Asn | Val | Thr | Val | Phe | Glu | Ala | Ala | Asp | Arg | | | |
| 65 | | | | | 70 | | | | | 75 | | | | | | | | |

| GCG | GGA | GGA | AAG | ATA | CGG | ACC | AAT | TCC | GAG | GGC | GGG | TTT | GTC | TGG | GAT | | | 348 |
| Ala | Gly | Gly | Lys | Ile | Arg | Thr | Asn | Ser | Glu | Gly | Gly | Phe | Val | Trp | Asp | | | |
| 80 | | | | | 85 | | | | | 90 | | | | | 95 | | | |

| GAA | GGA | GCT | AAC | ACC | ATG | ACA | GAA | GGT | GAA | TGG | GAG | GCC | AGT | AGA | CTG | | | 396 |
| Glu | Gly | Ala | Asn | Thr | Met | Thr | Glu | Gly | Glu | Trp | Glu | Ala | Ser | Arg | Leu | | | |
| | | | | 100 | | | | | 105 | | | | | 110 | | | | |

| ATT | GAT | GAT | CTT | GGT | CTA | CAA | GAC | AAA | CAG | CAG | TAT | CCT | AAC | TCC | CAA | | | 444 |
| Ile | Asp | Asp | Leu | Gly | Leu | Gln | Asp | Lys | Gln | Gln | Tyr | Pro | Asn | Ser | Gln | | | |
| | | | | 115 | | | | | 120 | | | | | 125 | | | | |

| CAC | AAG | CGT | TAC | ATT | GTC | AAA | GAT | GGA | GCA | CCA | GCA | CTG | ATT | CCT | TCG | | | 492 |
| His | Lys | Arg | Tyr | Ile | Val | Lys | Asp | Gly | Ala | Pro | Ala | Leu | Ile | Pro | Ser | | | |
| | | | 130 | | | | | 135 | | | | | 140 | | | | | |

| GAT | CCC | ATT | TCG | CTA | ATG | AAA | AGC | AGT | GTT | CTT | TCG | ACA | AAA | TCA | AAG | | | 540 |
| Asp | Pro | Ile | Ser | Leu | Met | Lys | Ser | Ser | Val | Leu | Ser | Thr | Lys | Ser | Lys | | | |
| | | | 145 | | | | | 150 | | | | | 155 | | | | | |

| ATT | GCG | TTA | TTT | TTT | GAA | CCA | TTT | CTC | TAC | AAG | AAA | GCT | AAC | ACA | AGA | | | 588 |
| Ile | Ala | Leu | Phe | Phe | Glu | Pro | Phe | Leu | Tyr | Lys | Lys | Ala | Asn | Thr | Arg | | | |
| 160 | | | | | 165 | | | | | 170 | | | | | 175 | | | |

| AAC | TCT | GGA | AAA | GTG | TCT | GAG | GAG | CAC | TTG | AGT | GAG | AGT | GTT | GGG | AGC | | | 636 |
| Asn | Ser | Gly | Lys | Val | Ser | Glu | Glu | His | Leu | Ser | Glu | Ser | Val | Gly | Ser | | | |
| | | | | 180 | | | | | 185 | | | | | 190 | | | | |

| TTC | TGT | GAA | CGC | CAC | TTT | GGA | AGA | GAA | GTT | GTT | GAC | TAT | TTT | GTT | GAT | | | 684 |
| Phe | Cys | Glu | Arg | His | Phe | Gly | Arg | Glu | Val | Val | Asp | Tyr | Phe | Val | Asp | | | |
| | | | 195 | | | | | 200 | | | | | 205 | | | | | |

| CCA | TTT | GTA | GCT | GGA | ACA | AGT | GCA | GGA | GAT | CCA | GAG | TCA | CTA | TCT | ATT | | | 732 |
| Pro | Phe | Val | Ala | Gly | Thr | Ser | Ala | Gly | Asp | Pro | Glu | Ser | Leu | Ser | Ile | | | |
| | | | 210 | | | | | 215 | | | | | 220 | | | | | |

| CGT | CAT | GCA | TTC | CCA | GCA | TTG | TGG | AAT | TTG | GAA | AGA | AAG | TAT | GGT | TCA | | | 780 |
| Arg | His | Ala | Phe | Pro | Ala | Leu | Trp | Asn | Leu | Glu | Arg | Lys | Tyr | Gly | Ser | | | |
| | | 225 | | | | | 230 | | | | | 235 | | | | | | |

| GTT | ATT | GTT | GGT | GCC | ATC | TTG | TCT | AAG | CTA | GCA | GCT | AAA | GGT | GAT | CCA | | | 828 |
| Val | Ile | Val | Gly | Ala | Ile | Leu | Ser | Lys | Leu | Ala | Ala | Lys | Gly | Asp | Pro | | | |
| 240 | | | | | 245 | | | | | 250 | | | | | 255 | | | |

| GTA | AAG | ACA | AGA | CAT | GAT | TCA | TCA | GGG | AAA | AGA | AGG | AAT | AGA | CGA | GTG | | | 876 |
| Val | Lys | Thr | Arg | His | Asp | Ser | Ser | Gly | Lys | Arg | Arg | Asn | Arg | Arg | Val | | | |
| | | | | 260 | | | | | 265 | | | | | 270 | | | | |

| TCG | TTT | TCA | TTT | CAT | GGT | GGA | ATG | CAG | TCA | CTA | ATA | AAT | GCA | CTT | CAC | | | 924 |

```
                                                                -continued

Ser Phe Ser Phe His Gly Gly Met Gln Ser Leu Ile Asn Ala Leu His
            275                 280                 285

AAT GAA GTT GGA GAT GAT AAT GTG AAG CTT GGT ACA GAA GTG TTG TCA      972
Asn Glu Val Gly Asp Asp Asn Val Lys Leu Gly Thr Glu Val Leu Ser
        290                 295                 300

TTG GCA TGT ACA TTT GAT GGA GTT CCT GCA CTA GGC AGG TGG TCA ATT     1020
Leu Ala Cys Thr Phe Asp Gly Val Pro Ala Leu Gly Arg Trp Ser Ile
305                 310                 315

TCT GTT GAT TCG AAG GAT AGC GGT GAC AAG GAC CTT GCT AGT AAC CAA     1068
Ser Val Asp Ser Lys Asp Ser Gly Asp Lys Asp Leu Ala Ser Asn Gln
320                 325                 330                 335

ACC TTT GAT GCT GTT ATA ATG ACA GCT CCA TTG TCA AAT GTC CGG AGG     1116
Thr Phe Asp Ala Val Ile Met Thr Ala Pro Leu Ser Asn Val Arg Arg
                340                 345                 350

ATG AAG TTC ACC AAA GGT GGA GCT CCG GTT GTT CTT GAC TTT CTT CCT     1164
Met Lys Phe Thr Lys Gly Gly Ala Pro Val Val Leu Asp Phe Leu Pro
            355                 360                 365

AAG ATG GAT TAT CTA CCA CTA TCT CTC ATG GTG ACT GCT TTT AAG AAG     1212
Lys Met Asp Tyr Leu Pro Leu Ser Leu Met Val Thr Ala Phe Lys Lys
        370                 375                 380

GAT GAT GTC AAG AAA CCT CTG GAA GGA TTT GGG GTC TTA ATA CCT TAC     1260
Asp Asp Val Lys Lys Pro Leu Glu Gly Phe Gly Val Leu Ile Pro Tyr
385                 390                 395

AAG GAA CAG CAA AAA CAT GGT CTG AAA ACC CTT GGG ACT CTC TTT TCC     1308
Lys Glu Gln Gln Lys His Gly Leu Lys Thr Leu Gly Thr Leu Phe Ser
400                 405                 410                 415

TCA ATG ATG TTC CCA GAT CGA GCT CCT GAT GAC CAA TAT TTA TAT ACA     1356
Ser Met Met Phe Pro Asp Arg Ala Pro Asp Asp Gln Tyr Leu Tyr Thr
                420                 425                 430

ACA TTT GTT GGG GGT AGC CAC AAT AGA GAT CTT GCT GGA GCT CCA ACG     1404
Thr Phe Val Gly Gly Ser His Asn Arg Asp Leu Ala Gly Ala Pro Thr
            435                 440                 445

TCT ATT CTG AAA CAA CTT GTG ACC TCT GAC CTT AAA AAA CTC TTG GGC     1452
Ser Ile Leu Lys Gln Leu Val Thr Ser Asp Leu Lys Lys Leu Leu Gly
        450                 455                 460

GTA GAG GGG CAA CCA ACT TTT GTC AAG CAT GTA TAC TGG GGA AAT GCT     1500
Val Glu Gly Gln Pro Thr Phe Val Lys His Val Tyr Trp Gly Asn Ala
465                 470                 475

TTT CCT TTG TAT GGC CAT GAT TAT AGT TCT GTA TTG GAA GCT ATA GAA     1548
Phe Pro Leu Tyr Gly His Asp Tyr Ser Ser Val Leu Glu Ala Ile Glu
480                 485                 490                 495

AAG ATG GAG AAA AAC CTT CCA GGG TTC TTC TAC GCA GGA AAT AGC AAG     1596
Lys Met Glu Lys Asn Leu Pro Gly Phe Phe Tyr Ala Gly Asn Ser Lys
                500                 505                 510

GAT GGG CTT GCT GTT GGA AGT GTT ATA GCT TCA GGA AGC AAG GCT GCT     1644
Asp Gly Leu Ala Val Gly Ser Val Ile Ala Ser Gly Ser Lys Ala Ala
            515                 520                 525

GAC CTT GCA ATC TCA TAT CTT GAA TCT CAC ACC AAG CAT AAT AAT TCA     1692
Asp Leu Ala Ile Ser Tyr Leu Glu Ser His Thr Lys His Asn Asn Ser
        530                 535                 540

CAT TGAAAGTGTC TGACCTATCC TCTAGCAGTT GTCGACAAAT TTCTCCAGTT          1745
His
    545

CATGTACAGT AGAAACCGAT GCGTTGCAGT TTCAGAACAT CTTCACTTCT TCAGATATTA   1805

ACCCTTCGTT GAACATCCAC CAGAAAGGTA GTCACATGTG TAAGTGGGAA AATGAGGTTA   1865

AAAACTATTA TGGCGGCCGA AATGTTCCTT TTTGTTTTCC TCACAAGTGG CCTACGACAC   1925

TTGATGTTGG AAATACATTT AAATTTGTTG AATTGTTTGA GAACACATGC GTGACGTGTA   1985
```

-continued

```
ATATTTGCCT ATTGTGATTT TAGCAGTAGT CTTGGCCAGA TTATGCTTTA CGCCTTTAAA       2045

AAAAAAAAAA AAAAAA                                                      2061
```

(2) INFORMATION FOR SEQ ID NO:8:

(i) SEQUENCE CHARACTERISTICS:
        (A) LENGTH: 544 amino acids
        (B) TYPE: amino acid
        (D) TOPOLOGY: linear (ii) MOLECULE TYPE: protein (xi) SEQUENCE DESCRIPTION: SEQ ID NO:8:

```
Met Leu Ala Leu Thr Ala Ser Ala Ser Ser Ala Ser Ser His Pro Tyr
 1               5                  10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Ala Ala Ala Tyr Arg Leu
        50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335
```

-continued

```
Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
        355                 360                 365

Met Asp Tyr Leu Pro Leu Ser Leu Met Val Thr Ala Phe Lys Lys Asp
    370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Gln Tyr Leu Tyr Thr Thr
                420                 425                 430

Phe Val Gly Gly Ser His Asn Arg Asp Leu Ala Gly Ala Pro Thr Ser
            435                 440                 445

Ile Leu Lys Gln Leu Val Thr Ser Asp Leu Lys Lys Leu Leu Gly Val
        450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495

Met Glu Lys Asn Leu Pro Gly Phe Phe Tyr Ala Gly Asn Ser Lys Asp
            500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Ser His
530                 535                 540
```

(2) INFORMATION FOR SEQ ID NO:9:

(i) SEQUENCE CHARACTERISTICS:
        (A) LENGTH: 1697 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 29..1501
        (D) OTHER INFORMATION: /note= "Yeast protox-3 cDNA;
        sequence from pWDC-5"

(xi) SEQUENCE DESCRIPTION: SEQ ID NO:9:

```
TTGGCATTTG CCTTGAACCA ACAATTCT ATG TCA ATT GCA ATT TGT GGA GGA     52
                              Met Ser Ile Ala Ile Cys Gly Gly
                                1               5

GGT ATA GCT GGT CTT AGT ACA GCA TTT TAT CTT GCT AGA TTG ATT CCA   100
Gly Ile Ala Gly Leu Ser Thr Ala Phe Tyr Leu Ala Arg Leu Ile Pro
    10                  15                  20

AAA TGT ACT ATT GAT TTG TAC GAA AAA GGT CCT CGT TTA GGT GGA TGG   148
Lys Cys Thr Ile Asp Leu Tyr Glu Lys Gly Pro Arg Leu Gly Gly Trp
25                  30                  35                  40

CTT CAG TCG GTC AAA ATC CCG TGT GCA GAT TCT CCA ACA GGA ACG GTT   196
Leu Gln Ser Val Lys Ile Pro Cys Ala Asp Ser Pro Thr Gly Thr Val
                45                  50                  55

TTG TTT GAG CAA GGT CCT AGA ACT CTT CGT CCT GCT GGG GTT GCT GGC   244
```

```
                Leu Phe Glu Gln Gly Pro Arg Thr Leu Arg Pro Ala Gly Val Ala Gly
                             60                  65                  70

TTA GCA AAC TTA GAT TTA ATT AGC AAG TTG GGC ATC GAA GAC AAG TTG              292
Leu Ala Asn Leu Asp Leu Ile Ser Lys Leu Gly Ile Glu Asp Lys Leu
             75                  80                  85

TTA AGG ATT TCG AGC AAT TCT CCC AGC GCA AAA AAC CGA TAT ATT TAT              340
Leu Arg Ile Ser Ser Asn Ser Pro Ser Ala Lys Asn Arg Tyr Ile Tyr
             90                  95                 100

TAC CCA GAT CGC TTA AAT GAA ATT CCT TCA AGC ATT TTA GGG AGT ATA              388
Tyr Pro Asp Arg Leu Asn Glu Ile Pro Ser Ser Ile Leu Gly Ser Ile
105                 110                 115                 120

AAG TCG ATT ATG CAG CCT GCT TTG CGT CCG ATG CCT TTG GCT ATG ATG              436
Lys Ser Ile Met Gln Pro Ala Leu Arg Pro Met Pro Leu Ala Met Met
                125                 130                 135

CTT GAG CCC TTT CGT AAA AGT AAG CGA GAT TCG ACA GAT GAA AGC GTG              484
Leu Glu Pro Phe Arg Lys Ser Lys Arg Asp Ser Thr Asp Glu Ser Val
                140                 145                 150

GGT TCA TTT ATG AGA AGA AGA TTT GGT AAA AAC GTT ACG GAT AGA GTT              532
Gly Ser Phe Met Arg Arg Arg Phe Gly Lys Asn Val Thr Asp Arg Val
            155                 160                 165

ATG AGT GCA ATG ATA AAT GGT ATT TAT GCT GGT GAT TTG AAT GAT TTG              580
Met Ser Ala Met Ile Asn Gly Ile Tyr Ala Gly Asp Leu Asn Asp Leu
170                 175                 180

TCT ATG CAT TCT AGC ATG TTT GGA TTT TTA GCG AAG ATT GAA AAA AAG              628
Ser Met His Ser Ser Met Phe Gly Phe Leu Ala Lys Ile Glu Lys Lys
185                 190                 195                 200

TAT GGA AAC ATT ACT TTG GGA TTA ATT AGA GCT CTT CTT GCA CGT GAA              676
Tyr Gly Asn Ile Thr Leu Gly Leu Ile Arg Ala Leu Leu Ala Arg Glu
                205                 210                 215

ATA TTA TCT CCT GCT GAG AAA GCT TTG GAA AGC AGC ACT ACT CGC AGA              724
Ile Leu Ser Pro Ala Glu Lys Ala Leu Glu Ser Ser Thr Thr Arg Arg
                220                 225                 230

GCC AAA AAC AGC AGA GCT GTC AAA CAG TAT GAA ATC GAC AAG TAT GTT              772
Ala Lys Asn Ser Arg Ala Val Lys Gln Tyr Glu Ile Asp Lys Tyr Val
            235                 240                 245

GCT TTC AAG GAA GGG ATT GAG ACT ATT ACA TTG TCA ATA GCA GAT GAA              820
Ala Phe Lys Glu Gly Ile Glu Thr Ile Thr Leu Ser Ile Ala Asp Glu
250                 255                 260

TTA AAA AAA ATG CCG AAT GTC AAG ATA CAT CTA AAC AAA CCG GCC CAA              868
Leu Lys Lys Met Pro Asn Val Lys Ile His Leu Asn Lys Pro Ala Gln
265                 270                 275                 280

ACT TTG GTT CCA CAT AAA ACT CAG TCT CTT GTA GAC GTC AAT GGT CAA              916
Thr Leu Val Pro His Lys Thr Gln Ser Leu Val Asp Val Asn Gly Gln
                285                 290                 295

GCT TAC GAG TAT GTT GTG TTT GCA AAC TCT TCT CGC AAT TTA GAG AAT              964
Ala Tyr Glu Tyr Val Val Phe Ala Asn Ser Ser Arg Asn Leu Glu Asn
                300                 305                 310

CTA ATA TCT TGT CCT AAA ATG GAA ACT CCG ACG TCG AGT GTT TAT GTC             1012
Leu Ile Ser Cys Pro Lys Met Glu Thr Pro Thr Ser Ser Val Tyr Val
            315                 320                 325

GTC AAC GTT TAT TAT AAG GAC CCT AAT GTT CTT CCA ATC CGT GGT TTT             1060
Val Asn Val Tyr Tyr Lys Asp Pro Asn Val Leu Pro Ile Arg Gly Phe
            330                 335                 340

GGG CTT TTG ATT CCA TCA TGC ACT CCA AAT AAT CCG AAT CAT GTT CTT             1108
Gly Leu Leu Ile Pro Ser Cys Thr Pro Asn Asn Pro Asn His Val Leu
345                 350                 355                 360

GGT ATC GTT TTT GAT AGT GAG CAA AAC AAC CCT GAA AAT GGA AGC AAG             1156
Gly Ile Val Phe Asp Ser Glu Gln Asn Asn Pro Glu Asn Gly Ser Lys
                365                 370                 375
```

```
GTC ACT GTC ATG ATG GGA GGG TCT GCT TAT ACA AAA AAT ACT TCT TTG    1204
Val Thr Val Met Met Gly Gly Ser Ala Tyr Thr Lys Asn Thr Ser Leu
            380                 385                 390

ATT CCA ACC AAC CCC GAA GAA GCC GTT AAC AAT GCT CTC AAA GCT TTG    1252
Ile Pro Thr Asn Pro Glu Glu Ala Val Asn Asn Ala Leu Lys Ala Leu
            395                 400                 405

CAG CAT ACT TTA AAA ATA TCC AGT AAG CCA ACA CTC ACG AAT GCA ACA    1300
Gln His Thr Leu Lys Ile Ser Ser Lys Pro Thr Leu Thr Asn Ala Thr
            410                 415                 420

TTA CAA CCA AAT TGC ATC CCT CAA TAT CGT GTT GGG CAT CAA GAT AAT    1348
Leu Gln Pro Asn Cys Ile Pro Gln Tyr Arg Val Gly His Gln Asp Asn
425                 430                 435                 440

CTT AAT TCT TTG AAA TCT TGG ATT GAG AAA AAT ATG GGA GGG CGA ATT    1396
Leu Asn Ser Leu Lys Ser Trp Ile Glu Lys Asn Met Gly Gly Arg Ile
                445                 450                 455

CTT CTA ACT GGA AGT TGG TAT AAT GGT GTT AGT ATT GGG GAT TGT ATT    1444
Leu Leu Thr Gly Ser Trp Tyr Asn Gly Val Ser Ile Gly Asp Cys Ile
            460                 465                 470

ATG AAT GGA CAT TCA ACA GCT CGA AAA CTA GCA TCA TTG ATG AAT TCT    1492
Met Asn Gly His Ser Thr Ala Arg Lys Leu Ala Ser Leu Met Asn Ser
            475                 480                 485

TCT TCT TGAGCGTTTA TAAATGTTGA TATAAAATTA GTATATAGTT CCTTTGATTA    1548
Ser Ser
    490

TTTTATGAGT TGAAAATGCC ACTTGTGAAA TAATTTTGCA CAAGCCCTTT TATTACAGAC    1608

GTATATGCGA GGACATTCGA CAAACGTTTG AAATTAAAAA TCATATGCCT TTTAGCTTAA    1668

GACATCAAGG TCATGAATAA TAAAATTTT                                      1697

(2) INFORMATION FOR SEQ ID NO:10:

(i) SEQUENCE CHARACTERISTICS:
        (A) LENGTH: 490 amino acids
        (B) TYPE: amino acid
        (D) TOPOLOGY: linear (ii) MOLECULE TYPE: protein (xi) SEQUENCE DESCRIPTION: SEQ ID NO:10:

Met Ser Ile Ala Ile Cys Gly Gly Gly Ile Ala Gly Leu Ser Thr Ala
  1               5                  10                  15

Phe Tyr Leu Ala Arg Leu Ile Pro Lys Cys Thr Ile Asp Leu Tyr Glu
                 20                  25                  30

Lys Gly Pro Arg Leu Gly Gly Trp Leu Gln Ser Val Lys Ile Pro Cys
             35                  40                  45

Ala Asp Ser Pro Thr Gly Thr Val Leu Phe Glu Gln Gly Pro Arg Thr
         50                  55                  60

Leu Arg Pro Ala Gly Val Ala Gly Leu Ala Asn Leu Asp Leu Ile Ser
 65                  70                  75                  80

Lys Leu Gly Ile Glu Asp Lys Leu Leu Arg Ile Ser Ser Asn Ser Pro
                 85                  90                  95

Ser Ala Lys Asn Arg Tyr Ile Tyr Tyr Pro Asp Arg Leu Asn Glu Ile
            100                 105                 110

Pro Ser Ser Ile Leu Gly Ser Ile Lys Ser Ile Met Gln Pro Ala Leu
        115                 120                 125

Arg Pro Met Pro Leu Ala Met Met Leu Glu Pro Phe Arg Lys Ser Lys
    130                 135                 140

Arg Asp Ser Thr Asp Glu Ser Val Gly Ser Phe Met Arg Arg Arg Phe
145                 150                 155                 160
```

```
Gly Lys Asn Val Thr Asp Arg Val Met Ser Ala Met Ile Asn Gly Ile
            165                 170                 175

Tyr Ala Gly Asp Leu Asn Asp Leu Ser Met His Ser Ser Met Phe Gly
            180                 185                 190

Phe Leu Ala Lys Ile Glu Lys Lys Tyr Gly Asn Ile Thr Leu Gly Leu
            195                 200                 205

Ile Arg Ala Leu Leu Ala Arg Glu Ile Leu Ser Pro Ala Glu Lys Ala
            210                 215                 220

Leu Glu Ser Ser Thr Thr Arg Ala Lys Asn Ser Arg Ala Val Lys
225                 230                 235                 240

Gln Tyr Glu Ile Asp Lys Tyr Val Ala Phe Lys Glu Gly Ile Glu Thr
            245                 250                 255

Ile Thr Leu Ser Ile Ala Asp Glu Leu Lys Lys Met Pro Asn Val Lys
            260                 265                 270

Ile His Leu Asn Lys Pro Ala Gln Thr Leu Val Pro His Lys Thr Gln
            275                 280                 285

Ser Leu Val Asp Val Asn Gly Gln Ala Tyr Glu Tyr Val Val Phe Ala
            290                 295                 300

Asn Ser Ser Arg Asn Leu Glu Asn Leu Ile Ser Cys Pro Lys Met Glu
305                 310                 315                 320

Thr Pro Thr Ser Ser Val Tyr Val Val Asn Val Tyr Tyr Lys Asp Pro
            325                 330                 335

Asn Val Leu Pro Ile Arg Gly Phe Gly Leu Leu Ile Pro Ser Cys Thr
            340                 345                 350

Pro Asn Asn Pro Asn His Val Leu Gly Ile Val Phe Asp Ser Glu Gln
            355                 360                 365

Asn Asn Pro Glu Asn Gly Ser Lys Val Thr Val Met Met Gly Gly Ser
            370                 375                 380

Ala Tyr Thr Lys Asn Thr Ser Leu Ile Pro Thr Asn Pro Glu Glu Ala
385                 390                 395                 400

Val Asn Asn Ala Leu Lys Ala Leu Gln His Thr Leu Lys Ile Ser Ser
            405                 410                 415

Lys Pro Thr Leu Thr Asn Ala Thr Leu Gln Pro Asn Cys Ile Pro Gln
            420                 425                 430

Tyr Arg Val Gly His Gln Asp Asn Leu Asn Ser Leu Lys Ser Trp Ile
            435                 440                 445

Glu Lys Asn Met Gly Gly Arg Ile Leu Leu Thr Gly Ser Trp Tyr Asn
            450                 455                 460

Gly Val Ser Ile Gly Asp Cys Ile Met Asn Gly His Ser Thr Ala Arg
465                 470                 475                 480

Lys Leu Ala Ser Leu Met Asn Ser Ser Ser
            485                 490

(2) INFORMATION FOR SEQ ID NO:11:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: oligonucleotide used to construct
            pCGN1761ENX (iii) HYPOTHETICAL: NO
```

-continued

```
    (iv) ANTI-SENSE: NO (xi) SEQUENCE DESCRIPTION: SEQ ID NO:11:

AATTATGACG TAACGTAGGA ATTAGCGGCC CGCTCTCGAG T                    41

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: oligonucleotide used to construct
            pCGN1761ENX (iii) HYPOTHETICAL: NO (iv) ANTI-SENSE: NO (xi) SEQUENCE DESCRIPTION: SEQ ID NO:12:

AATTACTCGA GAGCGGCCGC GAATTCCTAC GTTACGTCAT                      40
```

MANIPULATION OF PROTOPORPHYRINOGEN OXIDASE ENZYME ACTIVITY IN EUKARYOTIC ORGANISMS

CROSS-REFERENCE TO RELATED APPLICATIONS

This application is a continuation-in-part of U.S. application Ser. No. 08/261,198 filed Jun. 16, 1994 now abandoned.

FIELD OF THE INVENTION

The invention relates generally to the manipulation of the enzymatic activity responsible for the conversion of protoporphyrinogen IX to protoporphyrin IX in a biosynthetic pathway common to all eukaryotic organisms. In one aspect, the invention is applied to the development of herbicide resistance in plants, plant tissues and seeds. In another aspect, the invention is applied to the development of diagnostics and treatments for deficiencies in this enzymatic activity in animals, particularly humans.

BACKGROUND OF THE INVENTION

I. The Protox Enzyme and its Involvement in the Chlorophyll/Heme Biosynthetic Pathway The biosynthetic pathways which leads to the production of chlorophyll and heme share a number of common steps. Chlorophyll is a light harvesting pigment present in all green photosynthetic organisms. Heme is a cofactor of hemoglobin, cytochromes, P450 mixed-function oxygenases, peroxidases, and catalases (see, e.g. Lehninger, *Biochemistry*. Worth Publishers, New York (1975)), and is therefore a necessary component for all aerobic organisms.

The last common step in chlorophyll and heme biosynthesis is the oxidation of protoporphyrinogen IX to protoporphyrin IX. Protoporphyrinogen oxidase (referred to herein as "protox") is the enzyme which catalyzes this last oxidation step (Matringe et al., *Biochem. J.* 260: 231 (1989)).

The protox enzyme has been purified either partially or completely from a number of organisms including the yeast *Saccharomyces cerevisiae* (Labbe-Bois and Labbe, In *Biosynthesis of Heme and Chlorophyll*, E. H. Dailey, ed. McGraw Hill: New York, pp. 235–285 (1990)), barley etioplasts (Jacobs and Jacobs, *Biochem. J.* 244: 219 (1987)), and mouse liver (Dailey and Karr, *Biochem.* 26: 2697 (1987)). Genes encoding protox have been isolated from two prokaryotic organisms, *Escherichia coli* (Sasarrnan et al., *Can. J. Microbiol.* 39: 1155 (1993)) and *Bacillus subtilis* (Dailey et aL, *J. Biol. Chem.* 269: 813 (1994)). These genes share no sequence similarity; neither do their predicted protein products share any amino acid sequence identity. The *E. coli* protein is approximately 21 kDa, and associates with the cell membrane. The *B. subtilis* protein is 51 kDa, and is a soluble, cytoplasmic activity.

Presently, too little is known about the protox enzyme to allow isolation of protox encoding genes from higher eukaryotic organisms (i.e. animals, plants and all other multicellular nucleate organisms other than lower eukaryotic microorganisms such as yeast, unicellular algae, protozoans, etc.) using known approaches.

In particular, many of the standard techniques for isolation of new proteins and genes are based upon the assumption that they will be significantly similar in primary structure (i.e. amino acid and DNA sequence) to known proteins and genes that have the same function. Such standard techniques include nucleic acid hybridization and amplification by polymerase chain reaction using oligonucleotide primers corresponding to conserved amino acid sequence motifs. These techniques would not be expected to be useful for isolation of eukaryotic protox genes using present structural information which is limited to prokaryotic protox genes since there is no significant structural similarity even among the known prokaryotic protox genes and proteins.

Another approach that has been used to isolate biosynthetic genes in other metabolic pathways from higher eukaryotes is the complementation of microbial mutants deficient in the activity of interest. For this approach, a library of cDNAs from the higher eukaryote is cloned in a vector that can direct expression of the cDNA in the microbial host. The vector is then transformed or otherwise introduced into the mutant microbe, and colonies are selected that are phenotypically no longer mutant.

This strategy has worked for isolating genes from higher eukaryotes that are involved in several metabolic pathways, including histidine biosynthesis (e.g. U.S. patent application Ser. No. 08/061,644 to Ward et al., incorporated by reference herein in its entirety), lysine biosynthesis (e.g. Frisch et al., *Mol. Gen. Genet.* 228: 287 (1991)), purine biosynthesis (e.g. Aimi et al., *J. Biol. Chem.* 265: 9011 (1990)), and tryptophan biosynthesis (e.g. Niyogi et al., *Plant Cell* 5: 1011 (1993)). However, despite the availability of microbial mutants thought to be defective in protox activity (e.g. *E. coli* (Sasannan et al., *J. Gen. Microbiol.* 113: 297 (1979)), *Salmonella typhimurium* (Xu et al., *J. Bacteriol.* 174: 3953 (1992)), and *Saccharomyces cerevisiae* (Camadro et al,. *Biochem. Biophys. Res. Comm.* 106: 724 (1982)), application of this technique to isolate cDNAs encoding eukaryotic protox enzymatic activity is at best unpredictable based on the available information.

There are several reasons for this. First, the eukaryotic protox cDNA sequence may not be expressed at adequate levels in the mutant microbe, for instance because of codon usage inconsistent with the usage preferences of the microbial host. Second, the primary translation product from the cloned eukaryotic coding sequence may not produce a functional polypeptide, for instance if activity requires a post-translational modification, such as glycosylation, that is not carried out by the microbe. Third, the eukaryotic protein may fail to assume its active conformation in the microbial host, for instance if the protein is normally targeted to a specific organellar membrane system that the microbial host specifically lacks. This last possibility is especially likely for the plant protox enzyme, which is associated in the plant cell with organelles not present in microbial hosts used in the complementation assay. In particular, the plant protox enzyme is associated with both the chloroplast envelope and thylakoid membranes (Matringe et al., *J. Biol. Chem.* 267:4646 (1992)), and presumably reaches those membrane systems as a result of a post-translational targeting mechanism involving both an N-terminal transit sequence, and intrinsic properties of the mature polypeptide (see, e.g. Kohorn and Tobin, *Plant Cell* 1: 159 (1989); Li et al., *Plant Cell* 3: 709 (1991); Li et al., *J. Biol. Chem.* 267: 18999 (1992)).

II. Involvement of the Protox Gene in Animal/Human Disease Conditions

The protox enzyme is known to play a role in certain human disease conditions. Patients suffering from variegate porphyria, an autosomal dominant disorder characterized by both neuropsychiatric symptoms and skin lesions, have decreased levels of protox activity (Brenner and Bloomer, *New Engl. J. Med.* 302: 765 (1980)). Due to the lack of knowledge regarding the human protox enzyme and its corresponding gene, options for diagnosing and treating this disorder are presently very limited.

III. The Protox Gene as a Herbicide Target

The use of herbicides to control undesirable vegetation such as weeds or plants in crops has become almost a universal practice. The relevant market exceeds a billion dollars annually. Despite this extensive use, weed control remains a significant and costly problem for farmers.

Effective use of herbicides requires sound management. For instance, time and method of application and stage of weed plant development are critical to getting good weed control with herbicides. Since various weed species are resistant to herbicides, the production of effective herbicides becomes increasingly important.

Unfortunately, herbicides that exhibit greater potency, broader weed spectrum and more rapid degradation in soil can also have greater crop phytotoxicity. One solution applied to this problem has been to develop crops which are resistant or tolerant to herbicides. Crop hybrids or varieties resistant to the herbicides allow for the use of the herbicides without attendant risk of damage to the crop. Development of resistance can allow application of a herbicide to a crop where its use was previously precluded or limited (e.g. to pre-emergence use) due to sensitivity of the crop to the herbicide. For example, U.S. Pat. No. 4,761,373 to Anderson et al. is directed to plants resistant to various irnidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants that express a mutant acetolactate synthase which renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase(ACCase).

The protox enzyme serves as the target for a variety of herbicidal compounds. The herbicides that inhibit protox include many different structural classes of molecules (Duke et al., *Weed Sci*. 39: 465 (1991); Nandihalli et al., *Pesticide Biochem. Physiol*. 43: 193 (1992); Matringe et al., *FEBS Lett*. 245: 35 (1989); Yanase and Andoh, *Pesticide Biochem. Physiol*. 35: 70 (1989)). These herbicidal compounds include the diphenylethers {e.g. acifluorfen, 5-[2-chloro4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-[2,4-dichloro-5-(1-methylethoxy)phenyl]-5-(1,1-dimethylethyl)- 1,3,4-oxadiazol-2-(3H)-one), cyclic irnides (e.g. S-23142, N-(4-chloro-2-fluoro-5-propargyloxyphenyl)-3,4,5,6-tetrahydrophthalirnide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

The predicted mode of action of protox-inhibiting herbicides involves the accumulation of protoporphyrinogen IX in the chloroplast. This accumulation is thought to lead to leakage of protoporphyrinogen IX into the cytosol where it is oxidized by a peroxidase activity to protoporphyrin IX. When exposed to light, protoporphyrin IX can cause formation of singlet oxygen in the cytosol. This singlet oxygen can in turn lead to the formation of other reactive oxygen species, which can cause lipid peroxidation and membrane disruption leading to rapid cell death (Lee et al., *Plant Physiol*. 102: 881 (1993)).

Not all protox enzymes are sensitive to herbicides which inhibit plant protox enzymes. Both of the protox enzymes encoded by genes isolated from *Escherichia coli* (Sasarman et al., *Can. J. Microbiol*. 39: 1155 (1993)) and *Bacillus subtilis* (Dailey et al., *J. Biol. Chem*. 269: 813 (1994)) are resistant to these herbicidal inhibitors. In addition, mutants of the unicellular alga *Chiamydomonas reinhardtii* resistant to the phenylimide herbicide S-23142 have been reported (Kataoka et al., *J. Pesticide Sci*. 15: 449 (1990); Shibata et al., In *Research in Photosynthesis*, Vol.III, N. Murata, ed. Kluwer:Notherlands. pp. 567–570 (1992)). At least one of these mutants appears to have an altered protox activity that is resistant not only to the herbicidal inhibitor on which the mutant was selected, but also to other classes of protox inhibitors (Oshio et al., *Z. Naturforsch*. 48c: 339 (1993); Sato et al., In *ACS Symposium on Porphyric Pesticides*, S. Duke, ed. ACS Press: Washington, D.C. (1994)). A mutant tobacco cell line has also been reported that is resistant to the inhibitor S-21432 (Che et al.,. *Z. Naturforsch*. 48c: 350 (1993).

SUMMARY OF THE INVENTION

The present invention provides an isolated DNA molecule encoding the protoporphyrinogen oxidase (protox) enzyme from a eukaryotic organism. In particular, the present invention provides isolated DNA molecules encoding the protoporphyrinogen oxidase (protox) enzyme from a plant or human source.

Using the information provided by the present invention, the DNA coding sequence for the protoporphyrinogen oxidase (protox) enzyme from any eukaryotic organism may be obtained using standard methods.

In accordance with these discoveries, the present invention provides plants, plant tissues and plant seeds with altered protox activity which are resistant to inhibition by a herbicide at levels which normally are inhibitory to the naturally occurring protox activity in the plant. Plants encompassed by the invention include those which would be potential targets for protox inhibiting herbicides, particularly agronomically important crops such as maize and other cereal crops such as wheat, oats, rye, sorghum, rice, barley, millet, turf and forage grasses, and the like, as well as cotton, sugar cane, sugar beet, oilseed rape, and soybeans.

The present invention is directed further to methods for the production of plants, plant tissues, and plant seeds which contain a protox enzyme resistant to, or tolerant of inhibition by a herbicide at a concentration which inhibits the naturally occurring protox activity. One embodiment of the invention is directed to the preparation of transgenic maize plants, maize tissue or maize seed which have been stably transformed with a recombinant DNA molecule comprising a suitable promoter functional in plants operably linked to a structural gene encoding an unmodified prokaryotic protox enzyme which is resistant to the herbicide.

The invention is further directed to the preparation of transgenic plants, plant tissue and plant seed which has been stably transformed with a recombinant DNA molecule comprising a suitable promoter functional in plants operably linked to a structural gene encoding an unmodified eukaryotic protox enzyme. This results in over-expression of the unmodified protox in the plant sufficient to overcome inhibition of the enzyme by the herbicide.

The present invention also embodies the production of plants which express an altered protox enzyme tolerant of inhibition by a herbicide at a concentration which normally inhibits the activity of wild-type, unaltered protox. In this embodiment, the plant may be stably transformed with a recombinant DNA molecule comprising a structural gene encoding the resistant protox, or prepared by direct selection techniques whereby herbicide resistant lines are isolated, characterized and developed.

The present invention also embodies the recombinant production of the protox enzyme; and methods for using recombinantly produced protox. In particular, the present invention provides methods of using purified protox to screen for novel herbicides which affect the activity of protox, and to identify herbicide-resistant protox mutants. Genes encoding altered protox can be used as selectable markers in plant cell transformation methods.

The present invention is further directed to probes and methods for detecting the presence and form of the protox gene and quantitating levels of protox transcripts in an organism. These methods may be used to diagnose disease conditions which are associated with an altered form of the protox enzyme or altered levels of expression of the protox enzyme.

DETAILED DESCRIPTION OF THE INVENTION

In one aspect, the present invention is directed to an isolated DNA molecule which encodes a eukaryotic form of protoporphyrinogen oxidase (referred to herein as "protox"), the enzyme which catalyzes the oxidation of protoporphyrinogen IX to protoporphyrin IX. The DNA coding sequences and corresponding amino acid sequences for protox enzymes from *Arabidopsis thaliana* are provided as SEQ ID Nos. 1–4 and 9–10. The DNA coding sequences and corresponding amino acid sequences for maize protox enzymes are provided as SEQ ID Nos 5–8.

Any desired eukaryotic DNA encoding the protox enzyme may be isolated according to the invention. One method taught for isolating a eukaryotic protox coding sequence is represented by Example 1. In this method cDNA clones encoding a protox enzyme are identified from a library of cDNA clones derived from the eukaryote of interest based on their ability to supply protox enzymatic activity to a mutant host organism deficient in this activity. Suitable host organisms for use in this method are those which can be used to screen cDNA expression libraries and for which mutants deficient in protox activity are either available or can be routinely generated. Such host organisms include, but are not limited to, *E. coli* (Sasarrnan et al., *J. Gen. Microbiol.* 113: 297 (1979)), *Salmonella typhimurium* (Xu et al., *J. Bacteriol.* 174: 3953 (1992)), and *Saccharomyces cerevisiae* (Camadro et al. *Biochem. Biophys. Res. Comm.* 106: 724 (1982)).

Alternatively, eukaryotic protox coding sequences may be isolated according to well known techniques based on their sequence homology to the *Arabidopsis thaliana* (SEQ ID Nos. 1,3 and 9) and *Zea mays* (SEQ ID Nos. 5 and 7) protox coding sequences taught by the present invention. In these techniques all or part of the known protox coding sequence is used as a probe which selectively hybridizes to other protox coding sequences present in population of cloned genomic DNA fragments or cDNA fragments (i.e. genomic or cDNA libraries) from a chosen organism. Such techniques include hybridization screening of plated DNA libraries (either plaques or colonies; see, e.g. Sambrook et al., *Molecular Cloning*, eds., Cold Spring Harbor Laboratory Press. (1989)) and amplification by PCR using oligonucleotide primers corresponding to sequence domains conserved among known protox amino acid sequences (see, e.g. Innis et al., *PCR Protocols, a Guide to Methods and Applications eds.*, Academic Press (1990)). These methods are particularly well suited to the isolation of protox coding sequences from organisms related to the organism from which the probe sequence is derived. For example, application of these methods using the Arabidopsis or *Zea mays* coding sequence as a probe would be expected to be particularly well suited for the isolation of protox coding sequences from other plant species.

The isolated eukaryotic protox sequences taught by the present invention may be manipulated according to standard genetic engineering techniques to suit any desired purpose. For example, the entire protox sequence or portions thereof may be used as probes capable of specifically hybridizing to protox coding sequences and messenger RNAs. To achieve specific hybridization under a variety of conditions, such probes include sequences that are unique among protox coding sequences and are preferably at least 10 nucleotides in length, and most preferably at least 20 nucleotides in length. Such probes may be used to amplify and analyze protox coding sequences from a chosen organism via the well known process of polymerase chain reaction (PCR). This technique may be useful to isolate additional protox coding sequences from a desired organism or as a diagnostic assay to determine the presence of protox coding sequences in an organism and to associate altered coding sequences with particular adverse conditions such as autosomal dominant disorder in humans characterized by both neuropsychiatric symptoms and skin lesions, have decreased levels of protox activity (Brenner and Bloomer, *New Engl. J. Med.* 302: 765 (1980)).

Protox specific hybridization probes may also be used to map the location of the native eukaryotic protox gene(s) in the genome of a chosen organism using standard techniques based on the selective hybridization of the probe to genomic protox sequences. These techniques include, but are not limited to, identification of DNA polymorphisms identified or contained within the protox probe sequence, and use of such polymorphisms to follow segregation of the protox gene relative to other markers of known map position in a mapping population derived from self fertilization of a hybrid of two polymorphic parental lines (see e.g. Helentjaris et al., *Plant Mol. Biol.* 5: 109 (1985). Sommer et al. *Biotechniques* 12:82 (1992); D'Ovidio et al., *Plant Mol. Biol.* 15: 169 (1990)). While any eukaryotic protox sequence is contemplated to be useful as a probe for mapping protox genes from any eukaryotic organism, preferred probes are those protox sequences from organisms more closely related to the chosen organism, and most preferred probes are those protox sequences from the chosen organism. Mapping of protox genes in this manner is contemplated to be particularly useful in plants for breeding purposes. For instance, by knowing the genetic map position of a mutant protox gene that confers herbicide resistance, flanking DNA markers can be identified from a reference genetic map (see, e.g., Helentjaris, *Trends Genet.* 3: 217 (1987)). During introgression of the herbicide resistance trait into a new breeding line, these markers can then be used to monitor the extent of protox-linked flanking chromosomal DNA still present in the recurrent parent after each round of back-crossing.

Protox specific hybridization probes may also be used to quantitate levels of protox mRNA in an organism using standard techniques such as Northern blot analysis. This technique may be useful as a diagnostic assay to detect altered levels of protox expression that may be associated with particular adverse conditions such as autosomal dominant disorder in humans characterized by both neuropsychiatric symptoms and skin lesions, have decreased levels of protox activity (Brenner and Bloomer, *New Engl. J. Med.* 302: 765 (1980)).

For recombinant production of the enzyme in a host organism, the protox coding sequence may be inserted into an expression cassette designed for the chosen host and introduced into the host where it is recombinantly produced. The choice of specific regulatory sequences such as promoter, signal sequence, 5' and 3' untranslated sequences, and enhancer, is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189: 113 (1986); Brosius, *DNA* 8: 759 (1989)), yeast (see, e.g., Schneider and Guarente, *Meth. Enzymol.* 194: 373 (1991)) and insect cells (see, e.g., Luckow and Summers, *Bio/Technol.* 6: 47 (1988)). Specific examples include plasmids such as pBluescript (Stratagene, La Jolla, Calif.), PFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pVl 11392/Sf21 cells (Invitrogen, La Jolla, Calif.).

Recombinantly produced eukaryotic protox enzyme is useful for a variety of purposes. For example, it may be used to supply protox enzymatic activity in vitro. It may also be used in an in vitro assay to screen known herbicidal chemicals whose target has not been identified to determine if they inhibit protox. Such an in vitro assay may also be used as a more general screen to identify chemicals which inhibit protox activity and which are therefore herbicide candidates. Alternatively, recombinantly produced protox enzyme may be used to further characterize its association with known inhibitors in order to rationally design new inhibitory herbicides as well as herbicide tolerant forms of the enzyme.

Typically, the inhibitory effect on protox is determined by measuring fluorescence at about 622 to 635 nm, after excitation at about 395 to 410 nM (see, e.g. Jacobs and Jacobs, *Enyzme* 28: 206 (1982); Sherman et al., *Plant Physiol.* 97: 280 (1991)). This assay is based on the fact that protoporphyrin IX is a fluorescent pigment, and protoporphyrinogen IX is nonfluorescent. Protein extracts are prepared from selected subcellular fractions, e.g. etioplasts, mitochondria, microsomes, or plasma membrane, by differential centrifugation (see, e.g. Lee et al., *Plant Physiol.* 102:881 (1993); Prado et al, *Plant Physio.* 65: 956 (1979); Jackson and Moore, in *Plant Organelles.* Reid, ed., pp. 1–12; Jacobs and Jacobs, *Plant Physiol.* 101: 1181 (1993)). Protoporphyrinogen is prepared by reduction of protoporphyrin with a sodium amalgam as described by Jacobs and Jacobs (1982). Reactions mixtures typically consist of 100 mM Hepes (pH 7.5), 5 mM EDTA, 2 mM DTT, about 2 $\mu$M protoporphyrinogen IX, and about 1 mg/mL protein extract. Inhibitor solutions in various concentrations, e.g. 1 mM, 100 uM, 10 uM, 1 uM, 100 nM, 10 nM, 1 nM, 100 pM, are added to the enzyme extract prior to the initiation of the enzyme reaction. Once the protein extract is added, fluorescence is monitored for several minutes, and the slope of the slope (reaction rate) is calculated from a region of linearity. $IC_{50}$ is determined by comparing the slope of the inhibited reaction to a control reaction.

Another embodiment of the present invention involves the use of protox in an assay to identify inhibitor-resistant protox mutants. A typical assay is as follows:

(a) incubating a first sample of protox and its substrate, protoporphyrinogen IX, in the presence of a second sample comprising a protox inhibitor;

(b) measuring the enzymatic activity of the protox from step (a);

(c) incubating a first sample of a mutated protox and its substrate in the presence of a second sample comprising the same protox inhibitor;

(d) measuring the enzymatic activity of the mutated protox from step (c); and (e) comparing the enzymatic activity of the mutated protox with that provided by the unmutated protox.

The reaction mixture and the reaction conditions are the same as for the assay to identify inhibitors of protox (inhibitor assay) with the following modifications. First, a protox mutant, obtained as described above, is substituted in one of the reaction mixtures for the wild-type protox of the inhibitor assay. Second, an inhibitor of wild-type protox is present in both reaction mixtures. Third, mutated activity (enzyme activity in the presence of inhibitor and mutated protox) and unmutated activity (enzyme activity in the presence of inhibitor and wild-type protox) are compared to determine whether a significant increase in enzyme activity is observed in the mutated activity when compared to the unmutated activity. Mutated activity is any measure of enzymatic activity of the mutated protox enzyme while in the presence of a suitable substrate and the inhibitor. Unmutated activity is any measure of enzymatic activity of the wild-type protox enzyme while in the presence of a suitable-.substrate and the inhibitor. A significant increase is defined as an increase in enzymatic activity that is larger than the margin of error inherent in the measurement technique, preferably an increase by about 2-fold of the activity of the wild-type enzyme in the presence of the inhibitor, more preferably an increase by about 5-fold, most preferably an increase greater than by about 10-fold.

The herbicides that inhibit protox include many different structural classes of molecules (Duke et al., *Weed Sci.* 39: 465 (1991); Nandihalli et al., *Pesticide Biochem. Physiol.* 43: 193 (1992); Matringe et al., *FEBS Lett.* 245: 35 (1989); Yanase and Andoh, *Pesticide Biochem. Physiol.* 35: 70 (1989)), including the diphenylethers {e.g. acifluorifen, 5-[2-chloro-4-(trifluoromethyl)phenoxy]-2-nitrobezoic acid; its methyl ester; or oxyfluorfen, 2-chloro-1-(3-ethoxy4-nitrophenoxy)-4-(trifluorobenzene)}, oxidiazoles (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalirnide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)4-nitropyrazolyl-5-oxy] propionate; M&B 39279), pyridine derivatives (e.g. LS 82–556), and phenopylate and its O-phenylpyrrolidino- and piperidinocarbamate analogs.

The diphenylethers of particular significance are those having the general formula (Formula I)

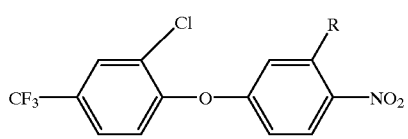

wherein R equals —COONa (Formula II), —CONHSO$_2$CH$_3$ (Formula III) or —COOCH$_2$COOC$_2$H$_5$ (Formula IV; see Maigrot et al., *Brighton Crop Protection Conference-Weeds*: 47–51 (1989)). Additional diphenylethers of interest are those where R equals:

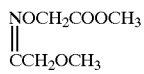

(Fornula IVa; see Hayashi et al., *Brighton Crop Protection Conference-Weeds*: 53–58 (1989)). An additional diphenylether of interest is one having the formula:

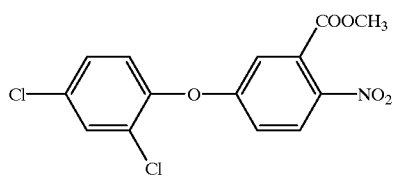

(Formula IVb; bifenox, see Dest et al., *Proc. Northeast Weed Sci. Conf.* 27: 31 (1973)).

Also of significance are the class of herbicides known as irnides, having the general formula (Formula V)

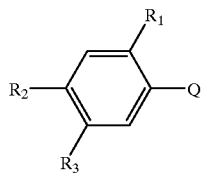

wherein Q equals (Formula VI)

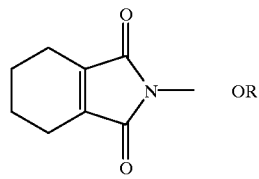

(Formula VII)

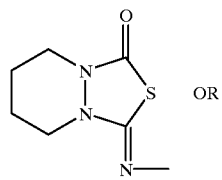

(Formula VIII)

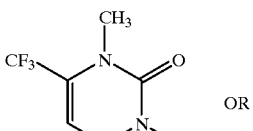

(Formula IX)

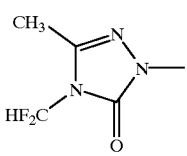

(Formula IXa)

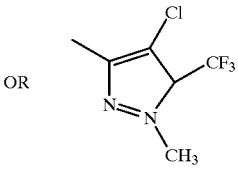

(Formula IXb)

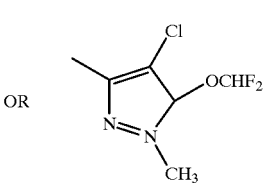

(see Hemper et al. (1995) in "Proceedings of the Eighth International Congress of Pesticide Chemistry", Ragdale et al., eds., Amer. Chem. Soc, Washington, D.C., pp.42–48 (1994));

and R$_1$ equals H, Cl or F, R$_2$ equals Cl and R$_3$ is an optimally substituted ether, thioether, ester, amino or alkyl group. Alternatively, R$_2$ and R$_3$ together may form a 5 or 6 membered heterocyclic ring. Examples of imide herbicides of particular interest are (Formula X)

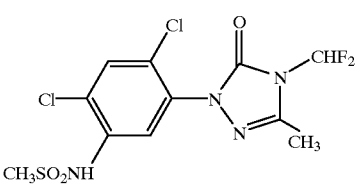

(Formula XI)

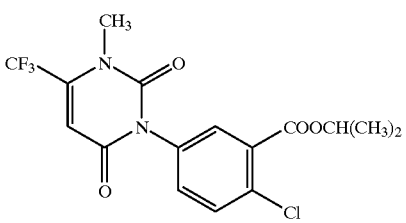

(Formula XII)

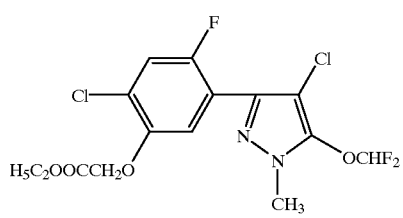

(see Miura et al., Brighton Crop Protection
Conference-Weeds: 35-40 (1993))

(Formula XIII)

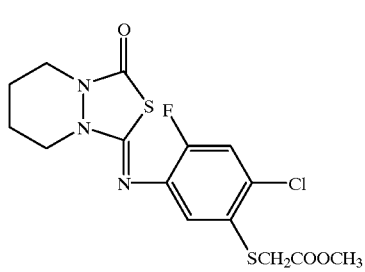

(Formula XIV)

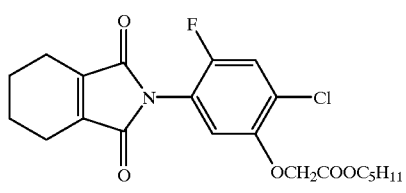

(Formula XV)

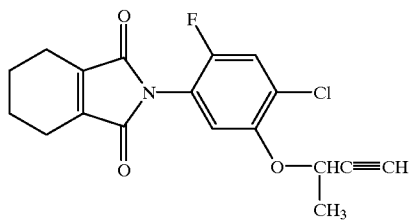

(Formula XVI)

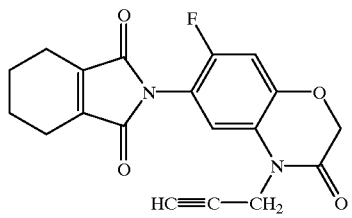

The herbicidal activity of the above compounds is described in the *Proceedings of the 1991 Brighton Crop Protection Conference, Weeds* (British Crop Protection Council) (Formulae X and XVI), *Proceedings of the 1993 Brighton Crop Protection Conference, Weeds* (British Crop Protection Council) (Formulae XII and XIII), U.S. Pat. No. 4,746,352 (Formula XI) and *Abstracts of the Weed Science Society of America* vol. 33, pg. 9 (1993)(Formula XIV).

The most preferred imide herbicides are those classified as aryluracils and having the general formula (Formula XVII)

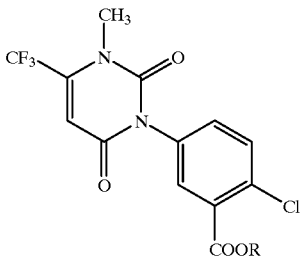

wherein R signifies the group ($C_{2-6}$-alkenyloxy)carbonyl-$C_{1-4}$-alkyl, as disclosed in U.S. Pat. No. 5,183,492, herein incorporated by reference.

Also of significance are herbicides having the general formula:

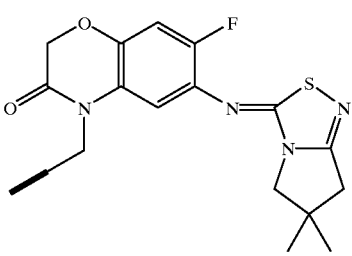

(Formula XVIII; thiadiazimin)
(see Weiler et al., Brighton Crop Protection Conference-
Weeds, pp. 29–34 (1993));

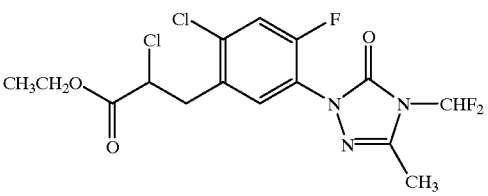

(Formula XIX; carfentrazone)
(see Van Saun et al., Brighton Crop Protection Conference-
Weeds: pp. 19–22 (1993));

N-substituted pyrazoles of the general formula:

(Formula XX)

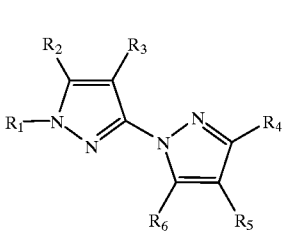

wherein $R_1$ is $C_1$–$C_4$-alkyl, optionally substituted by one or more halogen atoms;

$R_2$ is hydrogen, or a $C_1$–$C_4$-alkoxy, each of which is optionally substituted by one or more halogen atoms, or $R_1$ and $R_2$ together from the group —$(CH_2)_n$—X—, where X is bound at $R_2$;

$R_3$ is hydrogen or halogen, $R_4$ is hydrogen or $C_1$–$C_4$-alkyl, $R_5$ is hydrogen, nitro, cyano or the group —$COOR_6$ or —$CONR_7R_8$, and $R_6$ is hydrogen, $C_1$–$C_6$-alkyl, $C_2$–$C_6$-alkenyl or $C_2$–$C_6$-alkynyl; (see international patent publications WO 94/08999, WO 93/10100, and U.S. Pat. No. 5,405,829 assigned to Schering);

N-phenylpyrazoles, such as:

(Formula XXI; nipyraclofen)
(see page 621 of "The Pesticide Manual", 9th ed., ed. by C. R. Worthing, British Crop Protection Council, Surrey (1991));

and 3-substituted-2-aryl-4,5,6,7-tetrahydroindazoles (Lyga et al. *Pesticide Sci.* 42:29–36 (1994)).

Levels of herbicide which normally are inhibitory to the activity of protox include application rates known in the art, and which depend partly on external factors such as environment, time and method of application. For example, in the case of the imide herbicides represented by Formulae V through IX, and more particularly those represented by Formulae X through XVII, the application rates range from 0.0001 to 10 kg/ha, preferably from 0.005 to 2 kg/ha. This dosage rate or concentration of herbicide may be different, depending on the desired action and particular compound used, and can be determined by methods known in the art.

The present invention is further directed to plants, plant tissue and plant seeds tolerant to herbicides that inhibit the naturally occurring protox activity in these plants, wherein the tolerance is conferred by an altered protox enzyme activity. Representative plants include any plants to which these herbicides are applied for their normally intended purpose. Preferred are agronomically important crops, i.e., angiosperms and gymnosperms significant as cotton, soya, rape sugar beet, maize, rice, wheat, barley, oats, rye, sorghum, millet, turf, forage, turf grasses and the like.

By "altered protox enzyme activity" is meant a protox enzymatic activity different from that which naturally occurs in a plant (i.e. protox activity which occurs naturally in the absence of direct or indirect manipulation of such activity by man) which is resistant to herbicides that inhibit the naturally occurring activity. Altered protox enzyme activity may be conferred upon a plant according to the invention by increasing expression of wild-type, herbicide-sensitive protox, expressing an altered, herbicide-tolerant eukaryotic protox enzyme in the plant, expressing an unmodified or modified bacterial form of the protox enzyme which is herbicide resistant in the plant, or by a combination of these techniques.

Achieving altered protox enzyme activity through increased expression results in a level of protox in the plant cell at least sufficient to overcome growth inhibition caused by the herbicide. The level of expressed protox generally is at least two times, preferably five times, and more preferably at least ten times the natively expressed amount. Increased expression may be due to multiple copies of a wild-type protox gene; multiple occurrences of the protox coding sequence within the protox gene (i.e. gene amplification) or a mutation in the non-coding, regulatory sequence of the endogenous protox gene in the plant cell. Plants containing such altered protox enzyme activity can be obtained by direct selection in plants. This method is known in the art. See, e.g. Somers et al. in U.S. Pat. No. 5,162,602, and Anderson et al. in U.S. Pat. No. 4,761,373, and references cited therein. These plants also may be obtained via genetic engineering techniques known in the art. Increased expression of herbicide-sensitive protox also can be accomplished by stably transforming a plant cell with a recombinant or chimeric DNA molecule comprising a promoter capable of driving expression of an associated structural gene in a plant cell, linked to a homologous or heterologous structural gene encoding protox. By "homologous," it is meant that the protox gene is isolated from an organism taxonomically identical to the target plant cell. By "heterologous," it is meant that the protox gene is obtained from an organism taxonomically distinct from the target plant cell. Homologous protox genes can be obtained by complementing a bacterial or yeast auxotrophic mutant with a cDNA expression library from the target plant. See, e.g. Example 1 and Snustad et al, *Genetics* 120:1111–1114 (1988) (maize glutamine synthase); Delauney et al., *Mol. Genet.* 221:299–305 (1990) (soybean -pyrroline -5-carboxylate reductase); Frisch et al., *Mol. Gen. Genet.* 228:287–293 (1991) (maize dihydrodipicolinate synthase); Eller et al., *Plant Mol. Biol.* 18:557–566 (1992) (rape chloroplast 3-isopropylmalate dehydrogenase); *Proc. Natl. Acad. Sci, USA* 88:1731–1735 (1991); Minet et al., *Plant J.* 2:417–422 (1992) (dihydroorotate dehydrogenase) and references cited therein. Other known methods include screening genomic or cDNA libraries of higher plants, for example, for sequences that cross-hybridize with specific nucleic acid probes, or by screening expression libraries for the production of protox enzymes that cross-react with specific antibody probes. A preferred method involves complementing an *E. coli* hemG auxotrophic mutant with a maize or *Arabidopsis thaliana* cDNA library.

Examples of promoters capable of functioning in plants or plant cells, i.e., those capable of driving expression of the associated structural genes such as protox in plant cells, include the cauliflower mosaic virus (CaMV) 19S or 35S promoters and CAMV double promoters; nopaline synthase promoters; pathogenesis-related (PR) protein promoters; small subunit of ribulose bisphosphate carboxylase (ssuRUBISCO) promoters, and the like. Preferred are the rice actin promoter (McElroy et al., *Mol. Gen. Genet.* 231: 150 (1991)), maize ubiquitin promoter (EP 0 342 926; Taylor et al., *Plant Cell Rep.*12: 491 (1993)), and the Pr-1 promoter from tobacco, Arabidopsis, or maize (see U.S. patent application Ser. No. 08/181,271 to Ryals et al., incorporated by reference herein in its entirety). Also preferred are the 35S promoter and an enhanced or double 35S promoter such as that described in Kay et al., *Science* 236: 1299–1302 (1987) and the double 35S promoter cloned into pCGN2113, deposited as ATCC 40587, which are disclosed in each of commonly owned copending application Ser. No. 07/580,431, filed Sep. 7, 1990, which is a continuation-in-part of Ser. No. 07/425,504, filed Oct. 20, 1989, which is a continuation-in-part of Ser. No. 07/368,672, filed Jun. 20, 1989, which is a continuation-in-part of Ser. No. 07/329, 018, filed Mar. 24, 1989, the relevant disclosures of which are herein incorporated by reference in their entirety. The promoters themselves may be modified to manipulate promoter strength to increase protox expression, in accordance with art-recognized procedures.

Signal or transit peptides may be fused to the protox coding sequence in the chimeric DNA constructs of the invention to direct transport of the expressed protox enzyme to the desired site of action. Examples of signal peptides include those natively linked to the plant pathogenesis-related proteins, e.g. PR-1, PR-2, and the like. See, e.g., Payne et al., *Plant Mol. Biol.* 11:89–94 (1988). Examples of transit peptides include the chloroplast transit peptides such as those described in Von Heijne et al., *Plant Mol. Biol. Rep.* 9: 104–126 (1991); Mazur et al., *Plant Physiol.* 85: 1110 (1987); Vorst et al., *Gene* 65: 59 (1988), and mitochondrial transit peptides such as those described in Boutry et al., *Nature* 328:340–342 (1987). Chloroplast and mitochondrial transit peptides are contemplated to be particularly useful with the present ivention as protox enzymatic activity typically occurs within the mitochondria and chloroplast. Most preferred for use are chloroplast transit peptides as inhibition of the protox enzymatic activity in the chloroplasts is contemplated to be the primary basis for the action of protox-inhibiting herbicides (Witkowski and Halling, *Plant Physiol.* 87: 632 (1988); Lehnen et al., *Pestic. Biochem. Physiol.* 37: 239 (1990); Duke et al., *Weed Sci.* 39: 465 (1991)). Also included are sequences that result in localization of the encoded protein to various cellular compartments such as the vacuole. See, for example, Neuhaus et al., *Proc. Natl. Acad. Sci. USA* 88: 10362–10366 (1991) and Chrispeels, Ann. Rev. *Plant Physiol. Plant Mol. Biol.* 42: 21–53 (1991). The relevant disclosures of these publications are incorporated herein by reference in their entirety.

The chimeric DNA construct(s) of the invention may contain multiple copies of a promoter or multiple copies of the protox structural genes. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, β-glucuronidase, or β-galactosidase.

Altered protox enzyme activity may also be achieved through the generation or identification of modified forms of the isolated eukaryotic protox coding sequence having at least one amino acid substitution, addition or deletion which encode an altered protox enzyme resistant to a herbicide that inhibits the unaltered, naturally occuring form (i.e. forms which occur naturally in a eukaryotic organism without being manipulated, either directly via recombinant DNA methodology or indirectly via selective breeding, etc., by man). Genes encoding such enzymes can be obtained by numerous strategies known in the art. A first general strategy involves direct or indirect mutagenesis procedures on microbes. For instance, a genetically manipulable microbe, e.g. *E. coli* or *S. cerevisiae*, may be subjected to random mutagenesis in vivo, with, for example UV light or ethyl or methyl methane sulfonate. Mutagenesis procedures are described, for example in Miller, *Experiments in Molecular Genetics*, Cold Spring Harbor Laboratory, Cold Spring Harbor, N.Y. (1972); Davis et al., *Advanced Bacterial Genetics*, Cold Spring Harbor Laboratory, Cold Spring Harbor, N.Y. (1980); Sherman et al., *Methods in Yeast Genetics*, Cold Spring Harbor Laboratory, Cold Spring Harbor, N.Y. (1983); and U.S. Pat. No. 4,975,374 (Goodman et al). The microbe selected for mutagenesis contains a normally herbicide sensitive eukaryotic protox gene and is dependent upon the protox activity conferred by this gene. The mutagenized cells are grown in the presence of the herbicide at concentrations which inhibit the unmodified protox enzyme. Colonies of the mutagenized microbe that grow better than the unmutagenized microbe in the presence of the inhibitor (i.e. exhibit resistance to the inhibitor) are selected for further analysis. The protox genes from these colonies are isolated, either by cloning or by polymerase chain reaction amplification, and their sequences elucidated. Sequences encoding an altered protox enzyme are then cloned back into the microbe to confirm their ability to confer inhibitor resistance.

A second method of obtaining mutant herbicide-resistant alleles of the eukaryotic protox enzyme involves direct selection in plants. For example, the effect of a protox inhibitor such those as described above, on the growth inhibition of plants such as Arabidopsis, soybean, or maize may be determined by plating seeds sterilized by art-recognized methods on plates on a simple minimal salts medium containing increasing concentrations of the inhibitor. Such concentrations are in the range of 0.001,0.003, 0.01, 0.03,0.1,0.3, 1,3, 10,30, 110,300, 1000 and 3000 parts per million (ppm). The lowest dose at which significant growth inhibition can be reproducibly detected is used for subsequent experiments.

Mutagenesis of plant material may be utilized to increase the frequency at which resistant alleles occur in the selected population. Mutagenized seed material can be derived from a variety of sources, including chemical or physical mutagenesis or seeds, or chemical or physical mutagenesis or pollen (Neuffer, In *Maize for Biological Research*. Sheridan, ed. Univ.Press, Grand Forks, N.Dak., pp. 61–64 (1982)), which is then used to fertilize plants and the resulting $M_1$ mutant seeds collected. Typically, for Arabidopsis, $M_2$ seeds (Lehle Seeds, Tucson, Ariz.), i.e. progeny seeds of plants grown from seeds mutagenized with chemicals, such as ethyl methane sulfonate, or with physical agents, such as gamma rays or fast neutrons, are plated at densities of up to 10,000 seeds/plate (10 cm diameter) on minimal salts medium containing an appropriate concentration of inhibitor to select for resistance. Seedlings that continue to grow and remain green 7–21 days after plating are transplanted to soil and grown to maturity and seed set. Progeny of these seeds are tested for resistance to the herbicide. If the resistance trait is dominant, plants whose seed segregate 3:1::resistant:sensitive are presumed to have been heterozygous for the resistance at the $M_2$ generation. Plants that give rise to all resistant seed are presumed to have been homozygous for the resistance at the $M_2$ generation. Such mutagenesis on intact seeds and screening of their M2 progeny seed can also be carried out on other species, for instance soybean (see,e.g. U.S. Pat. No. 5,084,082 (Sebastian)). Mutant seeds to be screened for herbicide tolerance can also be obtained as-a result of fertilization with pollen mutagenized by chemical or physical means.

Two approaches can be taken to confirm that the genetic basis of the resistance is an altered protox gene. First, alleles of the protox gene from plants exhibiting resistance to the inhibitor can be isolated using PCR with primers based either upon conserved regions in the Arabidopsis and maize protox cDNA sequences shown in SEQ ID NOS: 1,3,5,7 below or, more preferably, based upon the unaltered protox gene sequences from the plant used to generate resistant alleles. After sequencing the alleles to determine the presence of mutations in the coding sequence, the alleles can be tested for their ability to confer resistance to the inhibitor on plants into which the putative resistance-conferring alleles have been transformed. These plants can be either Arabidopsis plants or any other plant whose growth is susceptible to the inhibitors. Second, the protox genes can be mapped relative to known restriction fragment length polymorphisms (RFLPs) (See, for example, Chang et al. *Proc. Natl. Acad, Sci, USA* 85:6856–6860 (1988); Nam et al., *Plant Cell* 1:699–705 (1989). The resistance trait can be independently mapped using the same markers. If resistance is due to a mutation in that protox gene, the resistance trait will map to a position indistinguishable from the position of a protox gene.

A third method of obtaining herbicide-resistant alleles of protox is by selection in plant cell cultures. Explants of plant tissue, e.g. embryos, leaf disks, etc. or actively growing callus or suspension cultures of a plant of interest are grown on defined medium lacking heme in the presence of increasing concentrations of the inhibitory herbicide or an analogous inhibitor suitable for use in a laboratory environment. Varying degrees of growth are recorded in different cultures. In certain cultures, fast-growing variant colonies arise that continue to grow even in the presence of normally inhibitory concentrations of inhibitor. The frequency with which such faster-growing variants occur can be increased by treatment with a chemical or physical mutagen before exposing the tissues or cells to the herbicide. Putative resistance-conferring alleles of the protox gene are isolated and tested as described in the foregoing paragraphs. Those alleles identified as conferring herbicide resistance may then be engineered for optimal expression and transformed into the plant. Alternatively, plants can be regenerated from the tissue or cell cultures containing these alleles.

A fourth method involves mutagenesis of wild-type, herbicide sensitive protox genes in bacteria or yeast, followed by culturing the microbe on medium that lacks heme, but which contains inhibitory concentrations of the inhibitor and then selecting those colonies that grow in the presence of the inhibitor. More specifically, a plant cDNA, such as the Arabidopsis or maize cDNA encoding protox is cloned into a microbe that otherwise lacks protox activity. Examples of such microbes include *E. coli, S. typhimurium*, and *S. cerevisiae* auxotrophic mutants, including *E. coli* strain SASX38 (Sasarman et al., *J. Gen. Microbiol.* 113: 297 (1979), *S. typhimurium* strain TE2483 or TT13680 (Xu et al., *J. Bacteriol.* 174: 3953 (1992)), and the hem14-1 yeast mutant (Camadro et al., *Biochem. Biophys. Res. Comm.* 106: 724 (1982)). The transformed microbe is then subjected to in vivo mutagenesis such as described immediately above, or to in vitro mutagenesis by any of several chemical or enzymatic methods known in the art, e.g. sodium bisulfite (Shortle et al., *Methods Enzymol.* 100:457–468 (1983); methoxylamine (Kadonaga et al., *Nucleic Acids Res.* 13:1733–1745 (1985); oligonucleotide-directed saturation mutagenesis (Hutchinson et al., *Proc. Natl. Acad. Sci. USA*, 83:710–714 (1986); or various polymerase misincorporation strategies (see, e.g. Shortle et al., *Proc. Natl. Acad. Sci. USA*, 79:1588–1592 (1982); Shiraishi et al., *Gene* 64:313–319 (1988); and Leung et al., *Technique* 1:11–15 (1989). Colonies that grow in the presence of normally inhibitory concentrations of inhibitor are picked and purified by repeated restreaking. Their plasmids are purified and tested for the ability to confer resistance to the inhibitor by retransforming them into the protox-lacking microbe. The DNA sequences of protox cDNA inserts from plasmids that pass this test are then determined.

Once a herbicide resistant protox allele is identified, it may be genetically engineered for optimal expression in a crop plant. This may include altering the coding sequence of the resistance allele for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); Koziel et al., *Bio/technol.* 11: 194 (1993)). Genetically engineering the protox allele for optimal expression may also include operably linking the appropriate regulatory sequences (i.e. promoter, signal sequence, transcriptional terminators). Preferred promoters will be those which confer high level constitutive expression or, more preferably, those which confer specific high level expression in the tissues susceptible to damage by the herbicide.

The recombinant DNA molecules can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., *BioTechniques* 4:320–334 (1986)), electroporation (Riggs et al, *Proc. Natl. Acad. Sci. USA* 83:5602–5606 (1986), Agrobacterium mediated transformation (Hinchee et al., *Biotechnology* 6:915–921 (1988)), direct s gene transfer (Paszkowski et al., EMBO J. 3:2717–2722 (1984)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926

(1988)). Also see, Weissinger et al., *Annual Rev. Genet.* 22:421477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl. Acad. Sci. USA*, 85:4305–4309 (1988)(maize); Klein et al., *Bio/Technology* 6:559–563 (1988)(maize); Klein et al., *Plant Physiol.* 91:440–444 (1988)(maize); Fromm et al., *Bio/Technology* 8:833–839 (1990); and Gordon-Kanim et al., *Plant Cell* 2:603–618 (1990)(maize).

Where a herbicide resistant protox allele is obtained via direct selection in a crop plant or plant cell culture from which a crop plant can be regenerated, it may be moved into commercial varieties using traditional breeding techniques to develop a herbicide tolerant crop without the need for genetically engineering the allele and transforming it into the plant. Alternatively, the herbicide resistant allele may be isolated, genetically engineered for optimal expression and then transformed into the desired variety.

Genes encoding altered protox resistant to a protox inhibitor can also be used as selectable markers in plant cell transformation methods. For example, plants, plant tissue or plant cells transformed with a transgene can also be transformed with a gene encoding an altered protox capable of being expressed by the plant. The thus-transformed cells are transferred to medium containing the protox inhibitor wherein only the transformed cells will survive. Protox inhibitors contemplated to be particularly useful as selective agents are the diphenylethers {e.g. acifluorfen, 5-[2-chloro4-(trifluoromethyl)phenoxy]-2-nitrobezoic acid; its methyl ester; or oxyfluorfen, 2-chloro-1-(3-ethoxy4-nitrophenoxy) 4(trifluorobenzene)}, oxidiazoles, (e.g. oxidiazon, 3-[2,4-dichloro-5-(1-methylethoxy)phenyl]-5-(1,1-dimethylethyl)-1,3,4-oxadiazol-2-(3H)-one, cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)4-nitropyrazolyl-5-oxy]propionate; M&B 39279), pyridine derivatives (e.g. LS 82-556), and phenopyiate and its O-phenylpyrrolidino- and piperidinocarbamate analogs. The method is applicable to any plant cell capable of being transformed with an altered protox-encoding gene, and can be used with any transgene of interest. Expression of the transgene and the protox gene can be driven by the same promoter functional on plant cells, or by separate promoters.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook. *Molecular Cloning: A Laboratory manual*, Cold Spring Harbor laboratory, Cold Spring Harbor, N.Y. (1982) and by T. J. Silhavy, M. L. Berman, and L. W. Enquist, *Experiments with Gene Fusions*, Cold Spring Harbor Laboratory, Cold Spring Harbor, N.Y. (1984).

Example 1

Isolation of Arabidopsis cDNAs Encoding Protox Genes by Functional Complementation of an *E. coli* Mutant.

An *Arabidopsis thaliana* (Landsberg) cDNA library in the plasmid vector pFL61 (Minet et al., *Plant J.* 2:417–422 (1992)) was obtained and amplified. A second Arabidopsis (Columbia) cDNA library in the UniZap lambda vector (Stratagene) was purchased and amplified as pBluescript plasmids by mass in vivo excision of the phage stock. The *E. coli* hemG mutant SASx38 (Sasarman et al., *J. Gen. Microbiol.* 113: 297 (1979)) was obtained and maintained on L media containing 20 mg/ml hematin (United States Biochemicals). The plasmid libraries were transformed into SASx38 by electroporation using the Bio-Rad Gene Pulser and the manufacturer's conditions. The cells were plated on L agar containing 100 mg/ml ampicillin at a density of approximately 500,000 transformants/10 cm plate. The cels were incubated at 37° C. for 40 hours in low light and selected for the ability to grow without the addition of exogenous heme. Heme prototrophs were recovered at a frequency of $400/10^7$ from the pFL61 library and at a frequency of $2/10^7$ from the pBluescript library. Plasmid DNA was isolated from 24 colonies for sequence analysis. Each of the 24 was retransformed into SASx38 to verify ability to complement.

Sequence analysis revealed two classes of putative protox clones. Nine were of the type designated "Protox-1." Each was derived from the same gene, and two were full-length clones. The cDNA is 1719bp in length and encodes a protein of molecular weight 57.7 kDa. The N-terminal peptide sequence has features characteristic of a chloroplast transit peptide of approximately 60 amino acids. A database search with the GAP program (Deveraux et al., *Nucleic Acids Res.* 12:387–395 (1984) reveals homology with the *B. subtilis* hemY (protox) protein (Hansson and Hederstedt 1992, Dailey et al., *J. Biol. Chem.* 269: 813 (1994)). The two proteins are 53% similar, 31% identical with regions of high homology, including the proposed dinucleotide binding domain of the hemY protein (Dailey et al., *J. Biol. Chem.* 269: 813 (1994)).

The other 15 cDNA clones were of the type designated "Protox-2". These also appeared to arise from a single gene. The apparently full-length cDNA is 1738bp in length and encodes a protein of molecular weight 55.6kD. The amino terminus is somewhat characteristic of a mitochondrial transit peptide. The Protox-2 protein has limited homology to Protox-1 (53% similar, 28% identical) and to the *B. subtilis* protox (50% similar, 27% identical).

Protox-1, in the pBluescript SK vector, was deposited Apr. 5, 1994 as pWDC-2 (NRRL #B-21238).

Protox-2, in the pFL61 vector, was deposited Apr. 5, 1994 as pWDC-1 (NRRL #B-21237).

The Arabidopsis cDNA encoding protox-1 contained in pWDC-2 and protox-2 contained in pWDC-1 are set forth in SEQ ID NOS:1 and 3, respectively, below.

Example 2

Isolation of Maize cDNAs Encoding Protox Genes by Functional Complementation of an *E. coli* Mutant.

A *Zea Mays* (B73 inbred) cDNA library in lambda Uni-Zap was purchased from Stratagene and converted to a pBluescript library by mass in vivo excision. A second custom-made UniZap maize cDNA library was purchased from Clontech, and similarly converted to pBluescript plasmids. Selection for functional protox genes from maize was just as described for the Arabidopsis libraries above in Example 1.

Two heme prototrophs in 107 transformants were isolated from the Stratagene library, shown to recomplement and sequenced. These cDNAs were identical and proved to be homologs of Arabidopsis Protox-1. This maize clone, designated MzProtox-1, is incomplete. The cDNA is 1698bp in length and codes only for the putative mature protox enzyme; there is no transitpeptide sequence and no initiating methionine codon. The gene is 68% identical to Arab Protox-1 at the nucleotide level and 78% identical (87% similar) at the amino acid level (shown in Table 1).

A single heme prototroph in $10^7$ transformants was obtained from the Clontech library, shown to recomplement, and sequenced. The cDNA appears to be complete, is 2061 bp in length and encodes a protein of 59 kDa. This clone is a maize homolog of Arabidopsis Protox-2 and is designated MzProtox-2. The gene is 58% identical to Arab Protox-2 at the nucleotide level and 58% identical (76% similar) at the amino acid level (shown in Table 2). The maize clone has an N-terminal sequence that is 30 amino acids longer than the Arabidopsis clone. As with the Arabidopsis clones, homology between the two maize protox genes is quite low, with only 31% identity between the two protein sequences.

MzProtox-1, in the pBluescript SK vector, deposited May 20, 1994 as pWDC-4 with the NRRL (#B-21260), shown in SEQ ID NO:5.

MzProtox-2, in the pBluescript SK vector, deposited May 20, 1994 as pWDC-3 with the NRRL (#B-21259), shown in SEQ ID NO:7.

Example 3

Isolation of Additional Protox Genes Based on Sequence Homology to Known Protox Coding Sequences A phage or plasmid library is plated at a density of approximately 10,000 plaques on a 10 cm Petri dish, and filter lifts of the plaques are made after overnight growth of the plants at 37 C. The plaque lifts are probed with one of the cDNAs set forth in SEQ ID NOS:1, 3, 5 or 7, labeled with 32P-dCTP by the random priming method by means of a PrimeTime kit (International Biotechnologies, Inc., New Haven, Conn.). Hybridization conditions are 7% sodium dodecyl sulfate (SDS), 0.5 M NaPO4 pH 7.0, 1 mM EDTA at 50 C. After hybridization overnight, the filters are washed with 2×SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain protox genes sequentially homologous to the known protox coding sequences from any other eukaryote, particularly other higher plant species.

An alignment of the predicted amino acid sequences of the respective proteins encoded by the sequences shown in SEQ ID NOS: 2 and 6 are set forth in Table 1. An alignment of the predicted amino acid sequences of the respective proteins encoded by the sequences shown in SEQ ID NOS: 4 and 8 are set forth in Table 2.

TABLE 1

Comparison of the Arabidopsis (SEQ ID No. 2) and Maize (SEQ ID No. 6) Protox-1 Amino Acid Sequences Percent Similarity: 87.137 Percent Identity: 78.008
Protox-1.Pep x Mzprotox-1.Pep

```
 51  GGTTITTDCVIVGGGISGLCIAQALATKHPDAAPNLIVTEAKDRVGGNII  100
       ..|||:|||||||||.||||||:|  :..:::|||:.|.||||.
  1  ....NSADCVVVGGGISGLCTAQALATRH..GVGDVLVTEARARPGGNIT   44

101  T..REENGFLWEEGPNSFQPSDPMLTMVVDSGLKDDLVLGDPTAPRFVLW  148
     |  |.|:|:|||||||||||||||:|||.|||||||||||:|||.|||||||
 45  TVERPEEGYLWEEGPNSFQPSDPVLTMAVDSGLKDDLVFGDPNAPRFVLW   94

149  NGKLRPVPSKLTDLPFFDLMSIGGKIRAGFGALGIRPSPPGREESVEEFV  198
     :|||||||||  .|||||||||||.||:|||:||||||.||||||||||
 95  EGKLRPVPSKPADLPFFDLMSIPGKLRAGLGALGIRPPPPGREESVEEFV  144

199  RRNLGDEVFERLIEPFCSGVYAGDPSKLSMKAAFGKVWKLEQNGGSIIGG  248
     |||||.||||||||||||||||||||||||||||||||:||:.||||||
145  RRNLGAEVFERLIEPFCSGVYAGDPSKLSMKAAFGKVWRLEETGGSIIGG  194

249  TFKAIQERKNAPKAERDPRLPKPQGQTVGSFRKGLRMLPEAISARLGSKV  298
     |:|.||||...||:.||:|||||.||||:||||||  |||:||...|||||
195  TIKTIQERSKNPKPPRDARLPKPKGQTVASFRKGLAMLPNAITSSLGSKV  244

299  KLSWKLSGITKLESGGYNLTYETPDGLVSVQSKSVVMTVPSHVASGLLRP  348
     ||||||.:|||  :. ||  |.||||:|:||||.|||:||:||.|||.:|||
245  KLSWKLTSITKSDDKGYVLEYETPEGVVSVQAKSVIMTIPSYVASNILRP  294
```

TABLE 1-continued

Comparison of the Arabidopsis (SEQ ID No. 2) and
Maize (SEQ ID No. 6) Protox-1 Amino Acid Sequences

```
349  LSESAANALSKLYYPPVAAVSISYPKEAIRTECLIDGELKGFGQLHPRTQ  398
     ||..||:|||::|||||||.:|||||||||.||||||||.||||||||.|
295  LSSDAADALSRFYYPPVAAVTVSYPKEAIRKECLIDGELQGFGQLHPRSQ  344

399  GVETLGTIYSSSLFPNRAPPGRILLLNYIGGSTNTGILSKSEGELVEAVD  448
     ||||||||||||||||||||.||:||||||||.||||||:||.|:|||||||
345  GVETLGTIYSSSLFPNRAPDGRVLLLNYIGGATNTGIVSKTESELVEAVD  394

449  RDLRKMLIKPNSTDPLKLGVRVWPQAIPQFLVGHFDILDTAKSSLTSSGY  498
     ||||||||.....||| |||||||||||||||||:|:|:.||..|...:||
395  RDLRKMLINSTAVDPLVLGVRVWPQAIPQFLVGHLDLLEAAKAALDRGGY  444

499  EGLFLGGNYVAGVALGRCVEGAYETAIEVNNFMSRYAYK*  538
     :|||||||||||||||||||||||||.| ::.:|:.:||||
445  DGLFLGGNYVAGVALGRCVEGAYESASQISDFLTKYAYK*  484
```

Identical residues are denoted by the vertical bar between the two sequences. Alignment is performed using the GAP[20] program described in Deveraux et al., *Nucleic Acids Res.* 12:387–395 (1984).

TABLE 2

Comparison of the Arabidopsis (SEQ ID No. 4) and
Maize (SEQ ID NO. 8) Protox-2 Amino Acid Sequences Percent Similarity: 75.889 Percent Identity: 57.905
Protox-2.Pep x Mzprotox-2.Pep

```
  1  ..........................MASGAVAD.HQIEAVSGKRVAV  21
                               .| |:|:  .: |..::.|||
  1  MLALTASASSASSHPYRHASAHTRRPRLRAVLAMAGSDDPRAAPARSVAV  50

22  VGAGVSGLAAAYKLKSRGLNVTVFEADGRVGGKLRSVMQNGLIWDEGANT  71
     |||||||||||:|: .|:|||||||.:|.|||:|. :.|::|||||||
 51  VGAGVSGLAAAYRLRQSGVNVTVFEAADRAGGKIRTNSEGGFVWDEGANT  100

72  MTEAEPEVGSLLDDLGLREKQQFPISQKKRYIVRNGVPVMLPTNPIELVT  121
     |||:| |.:.|:||||||.:|||:| ||.||||||::|.|.::|.:||.|:.
101  MTEGEWEASRLIDDLGLQDKQQYPNSQHKRYIVKDGAPALIPSDPISLMK  150

122  SSVLSTQSKFQILLEPFLWKK....KSSKVSDASAEESVSEFFQRHFGQE  167
     ||||||.||:..:::||||:||   .|:|||:. .|||:.| :||||.|
151  SSVLSTKSKIALFFEPFLYKKANTRNSGKVSEEHLSESVGSFCERHFGRE  200

168  VVDYLIDPFVGGTSAADPDSLSMKHSFPDLWNVEKSFGSIIVGAIRTKFA  217
     ||||::||||:|||.|||:||||::.||.||||||:..:|:|||| .|:|
201  VVDYFVDPFVAGTSAGDPESLSIRHAFPALWNLERKYGSVIVGAILSKLA  250

218  AKGGKSRDTKSSPGTKKGSRGSFSFKGGMQILPDTLCKSLSHDEINLDSK  267
     |||:. :. ...|.|.::.|.|||||.|||| | :.| ..::.|::.|:..
251  AKGDPVKTRHDSSGKRRNRRVSFSFHGGMQSLINALHNEVGDDNVKLGTE  300

268  VLSLS..YNSGSRQENWSLSCVSHNETQRQ...NPHYDAVIMTAPLCNVK  312
     ||||. :::.. :.||:|. |.:..::: |.:||||||||||:||:
301  VLSLACTFDGVPALGRWSISVDSKDSGDKDLASNQTFDAVIMTAPLSNVR  350

313  EMKVMKGGQPFQLNFLPEINYMPLSVLITTFTKEKVKRPLEGFGVLIPSK  362
     ||. |||.|. |:|||.::|:|||:::|.|.|:.||||||||||| |
351  RMKFTKGGAPVVLDFLPKMDYLPLSLMVTAFKKDDVKKPLEGFGVLIPYK  400

363  E.QKHGFKTLGTLFSSMMFPDRSPSDVHLYTTFIGGSRNQELAKASTDEL  411
     | ||||:|||||||||||||||.|.| .||||||:||:.:|| |.|. |
401  EQQKHGLKTLGTLFSSMMFPDRAPDDQYLYTTFVGGSHNRDLAGAPTSIL  450

412  KQVVTSDLQRLLGVEGEPVSVNHYYWRKAFPLYDSSYDSVMEAIDKMEND  461
     ||.|||||.:|||||:. |.| || .|||||: .|.||:|||:|||.:
451  KQLVTSDLKKLLGVEGQPTFVKHVYWGNAFPLYGHDYSSVLEAIEKMEKN  500

462  LPGFFYAGNHRGGLSVGKSIASGCKAADLVISYLESCSNDKKPNDSL*  509
     |||||||||::||.||. ||||:|||||.|||||.......:
501  LPGFFYAGNSKDGLAVGSVIASGSKAADLAISYLESHTKHNNSH*...  545
```

Example 4

Isolation of a Contaminating Yeast Protox Clone from an Arabidopsis cDNA Library In an effort to identify any rare cDNAs with protox activity, a second screen of the pFL61 Arabidopsis library was done as before, again yielding hundreds of complementing clones. Approximately 600 of these were patched individually onto gridded plates and incubated at 28° C. for 18 hours. Duplicate filter lifts were made onto Colony/Plaque screen (NEN) membranes according to the manufacturer's instructions. The Protox-1 and Protox-2 cDNAs were removed from their vectors by digestion with EcoRI/XhoI and by NotI, respectively. The inserts were separated by gel electrophoresis in 1.0% SeaPlaque GTG (FMC) agarose, excised, and $^{32}$P-labeled by random priming (Life Technologies). One set of lifts was hybridized with each probe. Hybridization and wash conditions were as described in Church and Gilbert, 1984.

Colonies (~20) that failed to show clear hybridization to Protox-1 or Protox-2 were amplified in liquid culture and plasmid DNA was prepared. The DNA's were digested with NotI, duplicate samples were run on a 1.0% agarose gel, and then Southern blotted onto a Gene Screen Plus (NEN) filter. Probes of the two known Protox genes were labeled and hybridized as before. There were two identical clones that were not Protox-1 or Protox-2. This clone was shown to recomplement the SASX38 mutant, although it grows very slowly, and was designated Protox-3.

Protox-3, in the pFL61 vector, was deposited Jun. 8, 1994 as pWDC-5 (NRRL #B-21280). This coding sequence has been determined to be derived from yeast DNA which was present as a minor contaminant in the Arabidopsis cDNA library. The yeast DNA encoding protox-3 contained in pWDC-5 is set forth in SEQ ID NO:9 below.

Example 5

Demonstration of Plant Protox Clone Sensitivity to Protox Inhibitory Herbicides in a Bacterial System.

Liquid cultures of Protox-1/SASx38, Protox-2/SASx38 and pBluescript/XL1-Blue were grown in L amp$^{100}$. One hundred microliter aliquots of each culture were plated on L amp$^{100}$ media containing various concentrations (1.0 nM–10 mM) of a protox inhibitory aryluracil herbicide of formula XVII. Duplicate sets of plates were incubated for 18 hours at 37° C. in either low light or complete darkness.

The protox$^+$ E. coli strain XL1-Blue showed no sensitivity to the herbicide at any concentration, consistent with reported resistance of the native bacterial enzyme to similar herbicides. The Protox-1/SASx38 was clearly sensitive, with the lawn of bacteria almost entirely eliminated by inhibitor concentrations as low as 10 nM. The Protox-2/SASx38 was also sensitive, but only at a higher concentration (10 µM) of the herbicide. The effect of the herbicide on both plant protox strains was most dramatic in low light, but was also apparent on plates maintained entirely in the dark. The toxicity of the herbicide was entirely eliminated by the addition of 20mg/ml hematin to the plates.

The different herbicide tolerance between the two plant Protox strains is likely the result of differential expression from these two plasmids, rather than any inherent difference in enzyme sensitivity. Protox-1/SASx38 grows much more slowly than Protox-2/SASx38 in any heme-deficient media. In addition, the MzProtox-2/SASx38 strain, with a growth rate comparable to Arab Protox-1/SASx38, is also very sensitive to herbicide at the lower (10–100 nM) concentrations. Initial characterization of the yeast Protox-3 clone indicated that it also is herbicide sensitive.

Example 6

Selecting for Plant Protox Genes Resistant to Protox-inhibitory Herbicides in the E. coli Expression System.

Inhibition of plant protox enzymes in a bacterial system is useful for large-scale screening for herbicide-resistant mutations in the plant genes. Initial dose response experiments, done by plating from liquid cultures, gave rise to high frequency "resistant" colonies even at high concentrations of herbicide. This resistance was not plasmid-borne, based on retransformation/herbicide sensitivity assay. Transforming Protox plasmids into the SASx38 mutant and plating directly onto plates containing herbicide reduces this background problem almost entirely.

The plant protox plasmids are mutagenized in a variety of ways, using published procedures for chemical (e.g. sodium bisulfite (Shortle et al., *Methods Enzymol.* 100:457468 (1983); methoxylamine (Kadonaga et al., *Nucleic Acids Res.* 13:1733–1745 (1985); oligonucleotide-directed saturation mutagenesis (Hutchinson et al., *Proc. Natl. Acad. Sci. USA*, 83:710–714 (1986); or various polymerase misincorporation strategies (see, e.g. Shortle et al., *Proc. Natl. Acad. Sci. USA*, 79:1588–1592 (1982); Shiraishi et al., *Gene* 64:313–319 (1988); and Leung et al., *Technique* 1:11–15 (1989)). The expected up-promoter mutants from whole-plasmid mutagenesis are eliminated by recloning the coding sequence into a wild-type vector and retesting. Given that higher expression is likely to lead to better growth in the absence of herbicide, a visual screen for coding sequence mutants is also possible.

Any plant protox gene expressing herbicide resistance in the bacterial system may be engineered for optimal expression and transformed into plants using standard techniques as described herein. The resulting plants may then be treated with herbicide to confirm and quantitate the level of resistance conferred by the introduced protox gene.

Example 7

Constructs for Expression of Herbicide-resistant Microbial Protox Gene(s) in Plants.

The coding sequences for the *B. subtilis* protox gene hemY (Hansson and Hederstedt, *J. Bacteriol.* 174: 8081 (1992); Dailey et al., *J. Biol. Chem.* 269: 813 (1994)) and for the *E. coli* protox gene hemG (Sasarman et al., *Can. J. Microbiol.* 39: 1155 (1993)) were isolated from laboratory strains by PCR amplification using standard conditions and flanking primers designed from the published sequences. These genes are known to code for herbicide-resistant forms of the protox enzyme.

Using standard techniques of overlapping PCR fusion (Ausubel et al., *Current Protocols in Molecular Biology*.

John Wiley & Sons, Inc. (1994)), both bacterial genes were fused to two different Arabidopsis chloroplast transit peptide sequences (CTPs). The first was the CTP from the acetohydroxy acid synthase (AHAS, Mazur et al., *Plant Physiol.* 85: 1110 (1987)), which should allow import into the stroma of the chloroplast. The second was from the Arabidopsis plastocyanin gene (Vorst et al., *Gene* 65: 59 (1988)), which has a bipartite transit peptide. The amino terminal portion of this CTP targets the protein into the chloroplast, where the carboxy terminus routes it into the thylakoid membranes. All four gene fusions were cloned behind the 2×35S promoter in a binary expression vector designed for production of transgenic plants by agrobacterium transformation.

Following isolation of the Arabidopsis and maize protox cDNAs, the chloroplast transit peptide from Protox-1 or MzProtox-1 may also be fused to the two bacterial protox proteins in the same manner as above.

The vectors described above may then be transformed into the desired plant species and the resulting transforrnants assayed for increased resistance to herbicide.

Example 8

Domain Switching Between Arabidopsis/*B. subtilis* Genes to Produce Chimeric, Herbicide Resistant Protox.

One approach that may be used to generate a protox gene which is both herbicide resistant and capable of providing effective protox enzymatic activity in a plant is to fuse portion(s) of a bacterial and plant protox gene. The resulting chimeric genes may then be screened for those which are capable of providing herbicide resistant protox activity in a plant cell. For instance, the Arabidopsis and the *B. subtilis* (hemY) protox peptide sequences are reasonably colinear with regions of high homology. The hemY coding sequence is cloned into pBluescript and tested for its ability to express herbicide-resistant protox activity in SASX38. Protox-1/hemY chimeric genes are constructed using fusion PCR techniques, followed by ligation back into the pBluescript vector. The initial exchange is approximately in the middle of the proteins. These fusions are tested for protox function by complementation, and then assayed for herbicide resistance by plating on herbicide with intact Protox-1 and hemY controls.

Example 9

Production of Herbicide-tolerant Plants by Overexpression of Plant Protox Genes.

To express the Arabidopsis or maize protein in transgenic plants, the appropriate full length cDNA was inserted into the plant expression vector pCGN1761ENX, which was derived from pCGN1761 as follows. pCGN1761 was digested at its unique EcoRI site, and ligated to a double-stranded DNA fragment comprised of two oligonucleotides of sequence 5' AAT TAT GAC GTA ACG TAG GAA TTA GCG GCCC GCT CTC GAG T 3' (SEQ ID NO: 11) and 5' AAT TAC TCG AGA GCG GCC GCG AAT TCC TAC GTT ACG TCA T 3' (SEQ ID NO: 12). The resulting plasmid, pCGN1761ENX, contained unique EcoRI, NotI, and XhoI sites that lie between a duplicated 35S promoter from cauliflower mosaic virus (Kay et al., *Science* 236:1299–1302 (1987)) and the 3' untranslated sequences of the tml gene of *Agrobacterium tumefaciens*. This plasmid is digested and ligated to a fragment resulting from restriction enzyme digestion of one of the plasmids bearing a protox cDNA, such that it carries the complete protox cDNA. From this plasmid is excised an XbaI fragment comprising the Arabidopsis protox cDNA flanked by a duplicated 35S promoter and the 3' untranslated sequences of the tml gene of *A. tumefaciens*. This XbaI fragment is inserted into the binary vector pCIB200 at its unique XbaI site, which lies between T-DNA border sequences. The resulting plasmid, designated pCIB200protox, is transformed into *A. tumefaciens* strain CIB542. See, e.g. Uknes et al., *Plant Cell* 5:159–169 (1993).

Leaf disks of *Nicotiana tabacum* cv. Xanthi-nc are infected with *A. tumefaciens* CEB542 harboring pCIB200IGPD as described by Horsch et al, *Science* 227: 1229 (1985). Kanamycin-resistant shoots from 15 independent leaf disks are transferred to rooting medium, then transplanted to soil and the resulting plants grown to maturity in the greenhouse. Seed from these plants are collected and germinated on MS agar medium containing kanamycin. Multiple individual kanarnycin resistant seedlings from each independent primary transfornant are grown to maturity in the greenhouse, and their seed collected. These seeds are germinated on MS agar medium containing kanamycin.

Plant lines that give rise to exclusively kanamycin resistant seedlings are homozygous for the inserted gene and are subjected to further analysis. Leaf disks of each of the 15 independent transgenic lines are excised with a paper punch and placed onto MS agar containing various increasing concentrations of a protox inhibitory herbicide.

After three weeks, two sets of 10 disks from each line were weighed, and the results recorded. Transgenic lines more resistant to the inhibitor than wild type, non-transformed plants are selected for further analysis.

RNA is extracted from leaves of each of these lines. Total RNA from each independent homozygous line, and from non-transgenic control plants, is separated by agarose gel electrophoresis in the presence of formaldehyde (Ausubel et al., *Current Protocols in Molecular Biology*, Wiley & Sons, New York (1987)). The gel is blotted to nylon membrane (Ausubel et al., supra.) and hybridized with the radiolabeled Arabidopsis protox cDNA. Hybridization and washing conditions are as described by Church and Gilbert, *Proc. Natl. Acad. Sci. USA* 81:1991–1995 (1984). The filter is autoradiographed, and intense RNA bands corresponding to the protox transgene are detected in all herbicide-tolerant transgenic plant lines.

To further evaluate resistance of the protox-overexpressing line, plants are grown in the greenhouse and treated with various concentrations of a protox-inhibiting herbicide.

Example 10

Growth of Tobacco Cell Suspension Cultures

Media:

MX 1: This medium consists of Murashige and Skoog ("MS", T. Murashige et al., *Physiol. Plant.* 15:473497, 1962) major salts, minor salts and Fe-EDTA (Gibco #

500–1117; 4.3 g/l), 100 mg/l myo-inositol, 1 mg/l nicotinic acid, 1 mg/l pyridoxine-HCl, 10 mg/l thiamine -HCl, 2–3 g/l sucrose, 0.4 mg/l 2,4-dichlorophenoxyacetic acid, and 0.04 mg/l kinetin, pH 5.8. The medium is sterilized by autoclaving.

N6: This medium comprises macroelements, microelements and Fe-EDTA as described by C -C. Chu et al., Scientia Sinica 18:659 (1975), and the following organic compounds: Pyridoxine-HCl (0.5 mg/l), thiamine-HCl (0.1 mg/l), nicotinic acid (0.5 mg/l), glycine (2.0 mg/l), and sucrose (30.0 g/l). The solution is autoclaved. The final pH is 5.6.

Remarks: Macroelements are made up as a 10× concentrated stock solution, and microelements as a 1000× concentrated stock solution. Vitamin stock solution is normally prepared 100× concentrated.

Suspension cultured cells of Nicotiana tabacum, line S3, are grown in liquid culture medium Mx1. 100 ml Erlenmeyer flasks containing 25 ml medium MX1 are inoculated with 10 ml of a cell culture previously grown for 7 days. Cells are incubated at 25° C. in the dark on an orbital shaker at 100 rpm (2 cm throw). Cells are subcultured at 7 day intervals by inoculating an aliquot sample into fresh medium, by decanting or pipetting off around 90% of the cell suspension followed by replenishing fresh medium to give the desired volume of suspension. 5–8 grams of fresh weight cell mass are produced within 10 days of growth from an inoculum of 250–350 mg cells.

Example 11

Production of Tobacco Cell Cultures Tolerant to Herbicidal Protox Inhibitors by Plating Cells on Solidified Selection Medium Cells are pregrown as in Example 10. Cells are harvested by allowing cells to sediment, or by brief centrifugation at 500×g, and the spent culture medium is removed. Cells are then diluted with fresh culture medium to give a cell density suitable for cell plating, about 10,000 colony forming units per ml. For plating, cells in a small volume of medium (approx. 1 ml) are evenly spread on top of solidified culture medium (MX1, 0.8% agar) containing the desired concentration of the inhibitor. About 20–30 ml of medium are used per 10 cm Petri plate. The suitable inhibitor concentration is determined from a dose-response curve (Example 14), and is at least twofold higher than the $IC_{50}$ of sensitive wild-type cells.

Culture plates containing cells spread onto selection medium are incubated under normal growth conditions at 25–28° C. in the dark until cell colonies are formed. Emerging cell colonies are transferred to fresh medium containing the inhibitor in the desired concentration.

In a preferred modification of the described method the pregrown suspension of cultured cells is first spread in a small volume of liquid medium on top of the solidified medium. An equal amount of warm liquid agar medium (1.2–1.6% agar) kept molten at around 40° C. is added and the plate gently but immediately swirled to spread the cells evenly over the medium surface and to mix cells and agar medium, before the medium solidifies.

Alternatively, the cells are mixed with the molten agar medium prior to spreading on top of the selection medium.

This method has the advantage that the cells are embedded and immobilized in a thin layer of solidified medium on top of the selection medium. It allows for better aeration of the cells as compared to embedding cells in the whole volume of 20–30 ml.

Example 12

Production of Tobacco Cell Cultures Tolerant to a Herbicidal Protox Inhibitor by Growing Cells in Liquid Selection Medium Cells cultured as in Example 10 are inoculated at a suitable cell density into liquid medium MX1 containing the desired concentration of a herbicidal protox inhibitor. Cells are incubated and grown as in Example 10. Cells are subcultured, as appropriate depending on the rate of growth, using fresh medium containing the desired inhibitor concentration after a period of 7–10 days.

Depending on the inhibitor concentration used, cell growth may be slower than in the absence of inhibitor.

Example 13

Production of Tobacco Cells with Enhanced Levels of Protox Enzyme

In order to obtain cell cultures or callus with enhanced levels of protox enzyme, suspension cultures or callus are transferred, in a step-wise manner, to increasingly higher concentrations of herbicidal protox inhibitor. In particular, the following steps are performed:

Cell colonies emerging from plated cells of Example 11 are transferred to liquid MX1 medium containing the same concentration of protox inhibitor as used in the selection according to Example 11 in order to form suspension cultures. Alternatively, selected cell suspension cultures of Example 12 are subcultured in liquid MX1 medium containing the same concentration of protox inhibitor as used for selection according to Example 12.

Cultures are subcultured 1–20 times at weekly intervals and are then subcultured into MX1 medium containing the next higher herbicide concentration. The cells are cultured for 1–10 subcultures in medium containing this higher concentration of herbicide. The cells are then transferred to MX1 medium containing the next higher concentration of herbicide.

Alternatively, pieces of selected callus of Example 11 are transferred to solidified MX1 medium supplemented with the desired herbicide concentration. Transfer to higher herbicide concentrations follows the procedure outlined in the preceding paragraph except that solidified medium is used.

Example 14

Measuring Herbicide Dose-dependent Growth of Cells in Suspension Cultures

In order to obtain a dose-response curve the growth of cells at different concentrations of herbicide is determined. Suspension culture cells of herbicidal protox inhibitor sensitive wild-type tobacco cells S3 and herbicide tolerant selected or transgenic cells S3 and herbicide tolerant selected or transgenic cells are pregrown in liquid medium as in Example 11 at a high cell density for 2–4 days. The cells are washed free of spent medium and fresh medium without herbicide is added to give the desired cell density (about 150 mg FW cells per ml of suspension). A sample of 2.5 ml of cell suspension, containing approx. 250–300 mg FW cells, is then inoculated into approx. 30 ml of liquid medium of desired herbicide concentration contained in a 100 ml Erlenmeyer flask. Care is taken to inoculate the same amount of cells into each flask. Each flask contains an equal volume of medium. 3–6 replicate flasks are inoculated per herbicide concentration. The herbicide concentration is selected from zero (=control), 0.1 ppb, 0.3 ppb, 1 ppb, 3 ppb, 10 ppb, 30 ppb, 100 ppb, 300 ppb, 1000 ppb, 3000 ppb, and 10,000 ppb. Several samples of inoculated cells are also taken at the time of inoculation to determine the mass of cells inoculated per flask.

Cells are then incubated for growth under controlled conditions at 28° in the dark for 10 days. The cells are harvested by pouring the contents of each flask onto a filter paper disk attached to a vacuum suction device to remove all liquid and to obtain a mass of reasonably dry fresh cells. The fresh mass of cells is weighed. The dry weight of samples may be obtained after drying.

Cell growth is determined and expressed as cell gain within 10 days and expressed as a percentage relative to cells grown in the absence of herbicide according to the formula: (final mass of herbicide-grown cells minus inoculum mass ×100 divided by final mass of cells grown without herbicide minus inoculum mass). $IC_{50}$ values are determined from graphs of plotted data (relative cell mass vs. herbicide concentration). $IC_{50}$ denotes the herbicide concentration at which cell growth is 50% of control growth (cells grown in the absence of herbicide).

In a modification of the method several pieces of callus derived from a herbicide resistant cell culture, as obtained in Examples 11 and 13, are transferred to solidified callus culture medium containing the different herbicide concentrations. Relative growth is determined after a culture. period of 2–6 weeks be weighing callus pieces and comparing to a control culture grown in medium without herbicide. However, the suspension method is preferred for its greater accuracy.

Example 15

Determination of Cross Tolerance

In order to determine the extent at which cells show tolerance to analogous or other herbicides, Example 14 is repeated by growing cells in increasing concentrations of chosen herbicides. The relative growth of the cells and their $IC_{50}$ value is determined for each herbicide for comparison.

Example 16

Determining the Stability of the Herbicide Tolerance Phenotype Over Time

In order to determine whether the herbicide tolerant phenotype of a cell culture is maintained over time, cells are transferred from herbicide containing medium to medium without herbicide. Cells are grown, as described in Example 10, in the absence of herbicide for a period of 3 months, employing regular subculturing at suitable intervals (7–10 days for suspension cultures; 3–6 weeks for callus cultures). A known quantity of cells is then transferred back to herbicide containing medium and cultured for 10 days (suspension cultures) or 4 weeks (callus cultures). Relative growth is determined as in Example 14.

Example 17

Induction and Culture of Embryogenic Callus from Corn Scutellum Tissue

Ears are harvested from self pollinated corn plants of the inbred line Funk 2717 12–14 days post pollination. Husks are removed and the ears are sterilized for about 15 minutes by shaking in a 20% solution of commercial Chlorox bleach with some drops of detergent added for better wetting. Ears are then rinsed several times with sterile water. All further steps are performed aseptically in a sterile air flow hood. Embryos of 1.5–2.5 mm length are removed from the kernels with a spatula and placed, embryo axis downwards, onto MS culture medium containing 2 mg/l 2,4-dichlorophenoxyacetic acid (2,4-D) and 3% sucrose, solidified with 0.24% Gelrite$^R$.

Embryogenic callus forms on the scutellum tissue of the embryos within 24 weeks of culture at about 28° C. in the dark. The callus is removed from the explant and transferred to fresh solidified MS medium containing 2 mg/l 2,4-D. The subculture of embryogenic callus is repeated at weekly intervals. Only callus portions having an embryogenic morphology are subcultured.

Example 18

Selection of Corn Cell Cultures Tolerant to Herbicidal Protox Inhibitors a) Selection using embrogenic callus:

Embryogenic callus of Example 17 is transferred to callus maintenance medium consisting of N6 medium containing 2 mg/l 2,4-D, 3% sucrose and protox inhibitor at a concentration sufficient to retard growth, but that does not affect the embyrogenicity of the culture, and solidified with 0.24% Gelrite$^R$. To increase the frequency of herbicide tolerant mutations, cultures can be pretreated before selection with a chemical mutagen, e.g. ethylmethane sulfonate, or a physical mutagen, e.g. UV light, at a concentration just below the concentration at which growth inhibition is detected, as determined in Example 14. Cultures are incubated at 28° C. in the dark. After 14 days growing callus is transferred to fresh medium of the same composition. Only cultures with the desired embryogenic morphology known as friable embryogenic callus of type II morphology are subcultured. Cultures are propagated by subculturing at weekly intervals for two to ten subcultures on fresh medium whereby only the fastest growing cultures are subcultured. The fast growing callus is then transferred to callus maintenance medium containing a protox inhibiting herbicide at a suitable concentration as defined in Example 11. When callus grows well on this herbicide concentration, usually after about five to ten weekly subcultures, the callus is transferred to callus maintenance medium containing a three-fold higher concentration of inhibitor, and subcultured until a well growing culture is obtained. This process is repeated using medium containing protox inhibitor at a concentration 10-fold higher than the original suitable concentration, and again with medium containing 20-fold and 40-fold higher concentrations.

When sufficient callus has been produced it is transferred to regeneration medium suitable for embryo maturation and plant regeneration. Embryogenic callus growing on each of the herbicide concentrations used is transferred to regeneration medium.

b) Selection usina embryogenic suspension cultures:

Embryogenic suspension cultures of corn Funk inbred line 2717 are established according to Example 24 and maintained by subculturing at weekly intervals to fresh liquid N6 medium containing 2 mg/l 2,4-D. To increase the frequency of herbicide tolerant mutations, cultures can be treated at this time with a chemical mutagen, e.g. ethylmethane sulfonate, at a concentration just below the concentration at which growth inhibition is detected, as determined in Example 14. For selection, the cultures are transferred to liquid N6 medium containing 2 mg/l 2,4-D and a concentration of inhibitor sufficient to retard growth, but that does not affect the embyrogenicity of the culture. Cultures are grown on a shaker at 120 rpm at 28° C. in the dark. At weekly intervals, the medium is removed and fresh medium added. The cultures are diluted with culture medium in accord with their growth to maintain about 10 ml of packed cell volume per 50 ml of medium. At each subculture, cultures are inspected and only fast growing cultures with the desired friable embryogenic morphology are retained for further subculture. After two to ten subcultures in N6 medium containing, cultures are increasing in growth rate at least two- to threefold per weekly subculture. The cultures are then transferred to N6 medium containing 2 mg/l 2,4-D and a three-fold higher dose of inhibitor than originally used. Growing cultures are repeatedly subcultured in this medium for another two to ten subcultures as described above. Fast growing cultures with the desired friable embryogenic morphology are selected for further subculture. Fast growing cultures are then transferred to N6 medium containing 2 mg 2,4-D and a ten-fold higher concentration of inhibitor than originally used, and the process of subculturing growing cultures with the desired friable embryogenic morphology is repeated for two to ten subcultures until fast growing cultures are obtained. These cultures are then transferred to N6 medium containing 2 mg/l 2,4-D and a 30-fold higher concentration of inhibitor than originally used.

For regeneration of plants from each embryogenic suspension culture selected with the mentioned herbicide concentration level, the cultures are first transferred onto N6 medium solidified with 0.24% Gelrite$^R$ and containing 2 mg/l 2,4-D and, optionally, the concentration of inhibitor in which the cultures have been growing, to produce embryogenic callus. The embryogenic callus is subcultured onto fresh callus maintenance medium until a sufficient amount of callus is obtained for regeneration. Only cultures with the desired embryogenic morphology are subcultured.

Example 19

Regeneration of Corn Plants form Selected Callus or Suspension Culture

Plants are regenerated from the selected embryogenic callus cultures of Example 13 by transferring to fresh regeneration medium. Regeneration media used are: 0N6 medium consisting of N6 medium lacking 2,4–3, or N61 consisting of N6 medium containing 0.25 mg/l 2,4-D and 10 mg/l kinetin (6-furfurylaminopurine), or N62 consisting of N6 medium containing 0.1 mg/l 2,4-D and 1 mg/l kinetin, all solidified with 0.24% Gelrite$^R$. Cultures are grown at 28° C. in the light (16 h per day of 10–100 $\mu$Einsteins/m$^2$sec from white fluorescent lamps). The cultures are subcultured every two weeks onto fresh medium. Plantlets develop within 3 to 8 weeks. Plantlets at least 2 cm tall are removed from adhering callus and transferred to root promoting medium. Different root promoting media are used. The media consist of N6 or MS medium lacking vitamins with either the usual amount of salts or with salts reduced to one half, sucrose reduced to 1 g/l, and further either lacking growth regulating compounds or containing 0.1 mg/l a-naphthaleneacetic acid. Once roots are sufficiently developed, plantlets are transplanted to a potting mixture consisting of vermiculite, peat moss and garden soil. At transplanting all remaining callus is trimmed away, all agar is rinsed off and the leaves are clipped about half. Plantlets are grown in the greenhouse initially covered for some days with an inverted clear plastic cup to retain humidity and grown with shading. After acclimatization plants are repotted and grown to maturity. Fertilizer Peters 20-20-20 is used to ensure healthy plant development. Upon flowering plants are pollinated, preferably self pollinated.

Example 20

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl Acids Res* 18: 1062 (1990), Spencer et al. *Theor Appl Genet* 79: 625–631(1990)), the hph gene which confers resistance to the antibiotic hygromycin (Blochinger & Diggelmann, *Mol Cell Biol* 4: 2929–2931), and the dhfr gene, which confers resistance to methotrexate (Bourouis et al., *EMBO J*. 2(7): 1099–1104 (1983)).

(1) Construction of Vectors Suitable for Agrobacterium Transformation

Many vectors are available for transformation using *Agrobacterium tumefaciens*. These typically carry at least one T-DNA border sequence and include vectors such as pBIN19 (Bevan, *Nucl. Acids Res*. (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, *J Bacteriol*. 164: 446–455

(1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also EP 0 332 104, example 19[1338]). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives Thereof

The binary vector pCIB10 contains a gene encoding kanamycin resistance for selection in plants, T-DNA right and left border sequences and incorporates sequences from the wide host-range plasmid pRK252 allowing it to replicate in both E. coli and Agrobacterium. Its construction is described by Rothstein et al., Gene 53: 153–161 (1987). Various derivatives of pCIB10 have been constructed which incorporate the gene for hygromycin B phosphotransferase described by Gritz et al., Gene 25: 179–188 (1983)). These derivatives enable selection of transgenic plant cells on hygromycin only (pCIB743), or hygromycin and kanamycin (pCB715, pCIB717). ps (2) Construction of Vectors Suitable for non-Agrobacterium Transformation.

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the E. coli GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from Streptomyces viridochromogenes was excised and inserted into the HpaI site of pCIB3060 (Thompson et al. EMBO J 6: 2519–2523 (1987)). This generated pCIB3064 which comprises the bar gene under the control of the CAMV 35S promoter and terminator for herbicide selection, a gene fro ampicillin resistance (for selection in E. coli) and a polylinker with the unique sites SphI, PstI, HindIII, and BamHI. This vector is suitable for the cloning of plant expression cassettes containing their own regulatory signals.

Construction of pSOG19 and pSOG35 pSOG35 is a transformation vector which utilizes the E. coli gene dihydrofolate reductase (DHFR) as a selectable marker conferring resistance to methotrexate. PCR was used to amplify the 35S promoter (~800 bp), intron 6 from the maize Adhl gene (~550 bp) and 18 bp of the GUS untranslated leader sequence from pSOG10. A 250 bp fragment encoding the E. coli dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 20

Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in Example 19.

Promoter Selection

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CAMV 35S terminator, the tml terminator, the nopaline synthase terminator, the pea rbcS E9 terminator. These can be used in both monocotyledons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res*. 15: 8693–8711 (1987); Skuzeski et al. Plant Molec. Biol. 15: 65–79 (1990))

Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins and which is cleaved during chloroplast import yielding the mature protein (e.g. Comai et al. *J. Biol. Chem*. 263: 15104–15109 (1988)). These signal sequences can be fused to heterologous gene products to effect the import of heterologous products into the chloroplast (van den Broeck et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. *Plant Molec. Biol*. 13: 411–418 (1989)). The cDNAs encoding these products can also be manipulated to effect the targeting of heterologous gene products to these organelles.

Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82: 6512–6516 (1985)).

In addition sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al., *Plant Molec. Biol*. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp 1081–1091(1982); Wasmann etal. *Mol. Gen. Genet*. 205:446–453 (1986)). These construction techniques are well known in the art and are equally applicable to mitochondria and peroxisomes. The choice of targeting which may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

Example 21

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. *Plant Cell* 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 22

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al., *Plant Cell* 2: 603–618 (1990)) and Fromm et al., *Biotechnology* 8: 833–839 (1990)) have published techniques for transformation of A188-derived maize line using particle bombardment. Furthermore, application WO 93/07278 (to Ciba-Geigy) and Koziel et al., *Biotechnology* 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics, helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Patent application Ser. No. 08/147,161 describes methods for wheat transformation and is hereby incorporated by reference.

Example 23

Selecting for Plant Protox Genes Resistant to Protox-inhibitory Herbicides in the E. coli Expression System The plasmid pWDC-4, encoding the maize chloroplastic protox enzyme, is transformed into the random mutagenesis strain XL1-Red (Stratagene, La Jolla, Calif.). The transformation is plated on L media containing 50 μg/ml ampicillin and incubated for 48 hours at 37° C. Lawns of transformed cells are scraped from the plates and plasmid DNA prepared using the Wizard Megaprep kit (Promega, Madison, Wis.). Plasmid DNA isolated from this mutator strain is predicted to contain approximately one random base change per 2000 nucleotides (see Greener et al., *Strategies* 7(2):32–34 (1994)).

The mutated plasmid DNA is transformed into the hemG mutant SASx38 (Sasarman et al., *J. Gen. Microbiol.* 113: 297 (1979) and plated on L media containing 100 μg/ml ampicillin and on the same media containing various concentrations of protox-inhibiting herbicide. The plates are incubated for 2–3 days at 37° C. Plasmid DNA is isolated from all colonies that grow in the presence of herbicide concentrations that effectively kill the wild type strain. The isolated DNA is then transformed into SASx38 and plated again on herbicide to ensure that the resistance is plasmid-borne.

Mutated pWDC-4 plasmid DNA is again isolated from resistant colonies and the protox coding sequence is excised by digestion with EcoRI and XhoI. The excised protox coding sequence is then recloned into an unmutagenized pBluescript vector and retested for resistance to protox-inhibiting herbicide in the same manner described above.

This process eliminates non-coding sequence mutations which confer resistance such as up-promoter mutants (i.e. mutants whose resistance is due to mutations causing increased expression of unmodified protox) and leaves only mutants whose resistance is due to mutations in the protox coding sequence. The DNA sequence for all putative herbicide-tolerant protox genes identified through this process is determined and mutations are identified by comparison with the wild-type pWDC-4 protox sequence.

Using the procedure described above, a resistance mutation converting a C to a T at nucleotide 498 in the pWDC-4 sequence (SEQ ID No. 5) has been identified. The plasmid carrying this mutation has been designated pMzC-1Val. This change converts a GCT codon for alanine at amino acid 166 (SEQ ID No. 6) to a GTT codon for valine and results in a protox enzyme that is at least 10× more resistant to protox-inhibiting herbicide in the bacterial assay.

pMzC-1Val, in the pBluescript SK vector, was deposited on Sep. 30, 1994 under the designation pWDC-8 with the Agricultural Research Culture Collection and given the deposit designation NRRL #21340.

The same strategy was used to screen for herbicide-resistant forms of the Arabidopsis Protox-1 gene in various vectors. One resistance mutation identified is a C to T change at nucleotide 689 in the pWDC-2 sequence (SEQ ID No. 1); this plasmid is designated pAraC-1Val. This change is identical to the pMzC-1Val mutant above, converting a GCT codon for alanine at amino acid 220 (SEQ ID No. 2) to a GTT codon for valine at the corresponding position in the Arabidopsis protox protein sequence.

A second resistant gene contains an A to G change at nucleotide 1307 in the pWDC-2 sequence (SEQ ID No. 1); this plasmid is designated pAraC-2Cys. This change converts TAC codon for tyrosine at amino acid 426 (SEQ ID No. 2) to a TGC codon for cysteine. The corresponding tyrosine codon in the maize protox-1 sequence at nucleotide position 1115–1117 (SEQ ID NO. 5; amino acid position 372 of SEQ ID NO. 6) may be similarly mutated to generate a herbicide resistant form of this enzyme.

A third resistant mutant has a G to A change at nucleotide 691 in the pWDC-2 sequence (SEQ ID No. 1); this plasmid is designated pAraC-3Ser. This mutation converts GGT codon for glycine at amino acid 221 SEQ ID No. 2) to an AGT codon for serine at the codon position adjacent to the mutation in pAraC-1. The corresponding glycine codon in the maize protox-1 sequence at nucleotide position 497–499 (SEQ ID NO. 5; amino acid position 167 of SEQ ID NO. 6) may be similarly mutated to generate a herbicide resistant form of this enzyme.

All the mutations described above result in a protox enzyme that is at least 10× more resistant to protox-inhibiting herbicide in the bacterial assay.

pAraC-2Cys, in the pFL61 vector, was deposited on Nov. 14, 1994 under the designation pWDC-7 with the Agricultural Research Culture Collection and given the deposit designation NRRL #21339N.

A. Additional Herbicide-resistant Codon Substitutions at Positions Identified in the Random Screen The amino acids identified as herbicide resistance sites in the random screen are replaced by other amino acids and tested for function and for herbicide tolerance in the bacterial system. Oligonucleotide-directed mutagenesis of the Arabidopsis Protox-1 sequence is performed using the Transformer Site-Directed Mutagenesis Kit (Clontech, Palo Alto, Calif.). After amino acid changes are confirmed by sequence analysis, the mutated plasmids are transformed into SASx38 and plated on L-amp[100] media to test for function and on various concentrations of protox-inhibiting herbicide to test for tolerance.

This procedure was applied to the alanine codon at nucleotides 688–690 and to the tyrosine codon at nucleotides 1306–1308 of the Arabidopsis protox sequence (SEQ ID No. 1). The results demonstrate that the alanine codon at nucleotides 688–690 can be changed to a codon for valine, threonine, leucine or cysteine to yield a herbicide-resistant protox enzyme which retains function. The results further demonstrate that the tyrosine codon at nucleotides 1306–1308 can be changed to a codon for cysteine, isoleucine, leucine, threonine or valine to yield a herbicide-resistant protox enzyme which retains function.

B. Demonstration of Resistant Mutations' Cross-tolerance to Various Protox-inhibiting Compounds.

Resistant mutant plasmids, selected for resistance against a single herbicide, are tested against a spectrum of other protox-inhibiting compounds. The SASx38 strain containing the wild-type plasmid is plated on a range of concentrations of each compound to determine the lethal concentration for each one. Resistant mutant plasmids in SASx38 are plated and scored for the ability to survive on a concentration of each compound which is at least 10 fold higher than the concentration that is lethal to the SASx38 strain containing the wild-type plasmid.

Results from cross-tolerance testing show that each of the mutations identified confer tolerance to a variety of protox inhibiting compounds. In particular, the results show that 1) the AraC1-Val mutation confers resistance to protox inhibitors including, but not necessarily limited to, those having the Formulae IV, XI, XIII, XIV, XV and XVII; 2) the AraC-2Cys mutation confers resistance to protox inhibitors including, but not necessarily limited to, those having Formulae XI, XIII, XV and XVII; 3) the MzC-1Val mutation confers resistance to protox inhibitors including, but not necessarily limited to, those having the Formulae XI, XII, XIII, XIV, XV, XVI and XVII; 4) the AraC-3Ser mutation confers resistance to protox inhibitors including, but not necessarily limited to, bifenox and those having the Formulae IV, XII, XIII, XIV, XV, and XVII.

C. Production of Herbicide Tolerant Plants by Overexpression of Plant Protox Genes The Arabidopsis Protox-1 coding sequences from both the wild-type and the resistant mutant AraC-1Val genes are excised by partial EcoRI and XhoI digestion and cloned into the pCGN1761ENX plant expression plasmid. The expression cassettes containing 2×35S-Protox gene fusions are excised by digestion with XbaI and cloned into the binary vector pCIB200. These binary protox plasmids are transformed by electroporation into Agrobacterium and then into Arabidopsis using the vacuum infiltration method (Bechtold et al., 1993). Transformants are selected on kanamycin, and T2 seed is generated from a number of independent lines. This seed is plated on GM media containing various concentrations of protox-inhibiting herbicide and scored for germination and survival. Multiple transgenic lines overexpressing either the wild type or the resistant mutant protox produce significant numbers of green seedlings on an herbicide concentration that is lethal to the empty vector control.

Various modifications of the invention described herein will become apparent to those skilled in the art. Such modifications are intended to fall within the scope of the appended claims.

We claim:

1. A probe which specifically hybridizes to a eukaryotic protoporphyrinogen oxidase gene or mRNA, wherein said probe comprises a contiguous portion of the coding sequence for a protoporphyrinogen oxidase from a eukaryote at least 10 nucleotides in length.

2. The probe of claim 1 wherein said coding sequence is selected from the group consisting of SEQ ID Nos. 1, 3, 5, 7 and 9.

3. The probe of claim 1 wherein said probe comprises a contiguous portion of the coding sequence for a protoporphyrinogen oxidase gene or mRNA that is derived from a plant.

4. The probe of claim 1 wherein said eukaryote is a plant.

5. A method for identifying a eukaryotic protoporphyrinogen oxidase gene or mRNA comprising, obtaining a sample containing nucleic acid molecules from a eukaryote, combining a probe of claim 1 with said sample under conditions wherein said probe binds specifically to a eukaryotic protoporphyrinogen oxidase gene or mRNA, isolating said probe bound to said eukaryotic protoporphyrinogen oxidase gene or mRNA.

6. The method of claim 5 wherein said probe is derived from a coding sequence selected from the group consisting of SEQ ID Nos. 1, 3, 5, 7 and 9.

7. The method of claim 5 wherein said probe comprises a contiguous portion of the coding sequence for a protoporphyrinogen oxidase from a plant.

* * * * *